(12) United States Patent
Suer et al.

(10) Patent No.: US 10,871,493 B2
(45) Date of Patent: Dec. 22, 2020

(54) ASSAY FOR THE DIAGNOSIS OF PEANUT ALLERGY

(71) Applicant: EUROIMMUN MEDIZINISCHE LABORDIAGNOSTIKA AG, Luebeck (DE)

(72) Inventors: Waltraud Suer, Buchholz (DE); Stefanie Rohwer, Kalkhorst (DE); Bettina Brix, Luebeck (DE); Alf Weimann, Luebeck (DE)

(73) Assignee: EUROIMMUN Medizinische Labordiagnostika AG, Luebeck (DE)

( * ) Notice: Subject to any disclaimer, the term of this patent is extended or adjusted under 35 U.S.C. 154(b) by 330 days.

(21) Appl. No.: 15/898,074

(22) Filed: Feb. 15, 2018

(65) Prior Publication Data

US 2018/0231567 A1    Aug. 16, 2018

(30) Foreign Application Priority Data

Feb. 15, 2017  (EP) ..................................... 17000245
Jun. 26, 2017  (EP) ..................................... 17001081

(51) Int. Cl.
| G01N 33/68 | (2006.01) |
|---|---|
| A61K 39/35 | (2006.01) |
| C07K 14/415 | (2006.01) |
| A61K 39/00 | (2006.01) |

(52) U.S. Cl.
CPC ......... *G01N 33/6854* (2013.01); *A61K 39/35* (2013.01); *C07K 14/415* (2013.01); *A61K 2039/577* (2013.01); *C07K 2319/00* (2013.01); *G01N 2800/24* (2013.01)

(58) Field of Classification Search
None
See application file for complete search history.

(56) References Cited

U.S. PATENT DOCUMENTS

| 7,745,391 | B2 | 6/2010 | Mintz et al. |
|---|---|---|---|
| 9,198,869 | B2 | 12/2015 | Walser et al. |
| 2006/0115499 | A1 | 6/2006 | Brimnes et al. |
| 2007/0275427 | A1 | 11/2007 | Akimoto et al. |
| 2009/0069236 | A1 | 3/2009 | Suck et al. |
| 2015/0301035 | A1 | 10/2015 | Meyer et al. |
| 2016/0310589 | A1 | 10/2016 | Arigon et al. |
| 2016/0320407 | A1 | 11/2016 | Ehlers et al. |
| 2017/0209566 | A1 | 7/2017 | Suer et al. |

FOREIGN PATENT DOCUMENTS

| EP | 1 440 979 | 7/2004 |
|---|---|---|
| EP | 1 475 662 | 9/2009 |
| JP | 5043077 | 7/2012 |
| WO | 2012/129246 | 9/2012 |
| WO | 2013/041540 | 3/2013 |
| WO | 2014/182932 | 11/2014 |
| WO | 2016/131000 | 8/2016 |
| WO | 2016/172511 | 10/2016 |

OTHER PUBLICATIONS

Office Action dated Nov. 4, 2019 in Canadian Application No. 2,992,044, 4 pages.
Office Action (Intention to Grant) issued in European Application No. 18 156 555.7 dated Oct. 9, 2019, 70 pages.
Office Action dated Dec. 17, 2019 in Japanese Application No. 2018-023758 with English translation, 8 pages.
Office Action dated Aug. 30, 2019 in Japanese Application No. 2018-023758 with English translation, 8 pages.
Office Action dated Apr. 8, 2019 in European Application No. 18 156 555.7, 5 pages.
Office Action dated Jan. 16, 2019 in Japanese Application No. 2018-023758 with English translation, 8 pages.
Van Erp, et al., 2016, CTOA, "Using Component-Resolve Diagnostics in the Management of Peanut-Allergic Patients", pp. 169-180.
Becker, et al., 2014, "Peanut Allergens", vol. 100, pp. 256-267.
Kieber-Janke, et al., 1999, "Selective Cloning of Peanut Allergens, Including Profilin and 2S Albumins, by Phage Display Technology", pp. 266-274.
Williams, et al., Jun. 2000, J Allergy Clin Immunol, "Analytic precision and accuracy of commercial immunoassays for specific IgE: Establishing a standard", pp. 1221-1230.
Taylor, et al., 2004, Olin Exp Allergy; 34:689-695, "A consensus protocol for the determination of the threshold doses for allergenic foods: how much is too much?".
Hausmann, et al., 2009, Immunol Allergy Olin., "The Basophil Activation Test in Immediate-Type Drug Allergy", pp. 555-566.
Raoult, et al., J. Immunol Methods 125, 1989 "The line blot: an immunoassay for monoclonal and other antibodies", pp. 57-65.
F. Codreanu, et al., 2011; 154(3), International Archives of Allergy and Immunology, "A Novel Immunoassay Using Recombinant Allergens Simplifies Peanut Allergy Diagnosis", pp. 216-226,.
Peeters, et al., 2007, Cli Exp Allergy; 37(1): 108-115; "Does skin prick test reactivity to purified allergenscorrelate with clinical severity of peanut allergy?".
Schmidt, et al., 2010, Journal of Proteome Research; "Detection and Structural Characterization of Natural Ara h 7, the Third Peanut Allergen of the 2S Albumin Family", pp. 3701-3709.
M.P. de Leon, et al., 2007; Molecular Immunology 44, "IgE cross-reactivity between the major peanut allergen Ara h 2 and tree nut allergens";, pp. 463-471.
Flinterman, et ai., 2007, Clinical and Experimental Allergy, 37, pp. 1221-1228, "Children with peanut allergy recognize predominantly Ara h2 and Ara 116, which remains stable over time".
M.A. Blankestijn, et al., "Specific IgE to peanut 2S Albumin Ara h 7 has a discriminative ability comparable to Ara h 2 and 6". Clin Exp Allergy. 2017;1-6.

(Continued)

*Primary Examiner* — Changhwa J Cheu
(74) *Attorney, Agent, or Firm* — Grüneberg and Myers PLLC

(57) ABSTRACT

A diagnostically useful carrier has a polypeptide for specifically capturing an antibody to Ara h 7 isotype 7.0201 in a sample from a subject. A method includes detecting in a sample from a subject the presence or absence of an antibody to Ara h 7 isotype 7.0201. A pharmaceutical composition includes Ara h 7 isotype 7.0201 or a variant thereof.

23 Claims, 4 Drawing Sheets

Specification includes a Sequence Listing.

(56) References Cited

OTHER PUBLICATIONS

Office Action dated Jan. 6, 2020 in Chinese Application No. 201711468054.0 with English translation, 23 pages.
Bublin et al., Curr Allergy Asthma Rep (2014) 14:426 (12 pages).
Hong et al., Journal of Food Safety and Quality, vol. 6 No. 1, Jan. 2015 with English translation (17 pages).
Office Action dated Jan. 21, 2020 in Indian Application No. 201734044678, bilingual, with English, 8 pages.
Office Action dated Jun. 30, 2020 in Chinese Application No. 201711468054.0 with English translation, 22 pages.
Office Action dated Jul. 6, 2020 in Korean Application No. 10-2018-0017527 with English translation, 21 pages.

IgE reactivity of 13 positive sera against peptides of Ara h 7.0201

Serum 1
Serum 2
Serum 3
cutoff

IgE reactivity of 13 negative sera against peptides of Ara h 7.0201

Serum 4
Serum 5
cutoff

Fig. 4

SEQUENCE LISTING

<160> NUMBER OF SEQ ID NOS: 17

<210> SEQ ID NO 1
<211> LENGTH: 139
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: SEQ ID NO 1 (expressed sequence without signal
      sequence of Ara h 7.0101)

<400> SEQUENCE: 1

Thr Arg Trp Asp Pro Asp Arg Gly Ser Arg Gly Ser Arg Trp Asp Ala
1               5                   10                  15

Pro Ser Arg Gly Asp Asp Gln Cys Gln Arg Gln Leu Gln Arg Ala Asn
            20                  25                  30

Leu Arg Pro Cys Glu Glu His Met Arg Arg Arg Val Glu Gln Glu Gln
        35                  40                  45

Glu Gln Glu Gln Asp Glu Tyr Pro Tyr Ser Arg Arg Gly Ser Arg Gly
    50                  55                  60

Arg Gln Pro Gly Glu Ser Asp Glu Asn Gln Glu Gln Arg Cys Cys Asn
65                  70                  75                  80

Glu Leu Asn Arg Phe Gln Asn Asn Gln Arg Cys Met Cys Gln Ala Leu
                85                  90                  95

Gln Gln Ile Leu Gln Asn Gln Ser Phe Trp Val Pro Ala Gly Gln Glu
            100                 105                 110

Pro Val Ala Ser Asp Gly Glu Gly Ala Gln Glu Leu Ala Pro Glu Leu
        115                 120                 125

Arg Val Gln Val Thr Lys Pro Leu Arg Pro Leu
    130                 135

<210> SEQ ID NO 2
<211> LENGTH: 144
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: SEQ ID NO 2 (expressed sequence without signal
      sequence of Ara h 7.0201)

<400> SEQUENCE: 2

Thr Arg Trp Asp Pro Asp Arg Gly Ser Arg Gly Ser Arg Trp Asp Ala
1               5                   10                  15

-continued

Pro Ser Arg Gly Asp Asp Gln Cys Gln Arg Gln Leu Gln Arg Ala Asn
            20                  25                  30

Leu Arg Pro Cys Glu Glu His Ile Arg Gln Arg Val Glu Lys Glu Gln
        35                  40                  45

Glu Gln Glu Gln Asp Glu Tyr Pro Tyr Ile Arg Gly Ser Arg Gly
    50                  55                  60

Gln Arg Pro Gly Glu Ser Asp Glu Asp Gln Glu Gln Arg Cys Cys Asn
65                  70                  75                  80

Glu Leu Asn Arg Phe Gln Asn Asn Gln Arg Cys Met Cys Gln Ala Leu
                85                  90                  95

Gln Gln Ile Leu Gln Asn Gln Ser Phe Arg Phe Gln Asp Arg Ser
        100                 105                 110

Gln Leu His Gln Met Glu Arg Glu Leu Arg Asn Leu Pro Gln Asn Cys
            115                 120                 125

Gly Phe Arg Ser Pro Ser Arg Cys Asp Leu Ser Ser Arg Thr Pro Tyr
    130                 135                 140

<210> SEQ ID NO 3
<211> LENGTH: 138
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: SEQ ID NO 3 (expressed sequence without signal
      sequence of Ara h 7.0)

<400> SEQUENCE: 3

Thr Arg Trp Asp Pro Asp Arg Gly Ser Arg Gly Leu Arg Trp Asp Ala
1               5                   10                  15

Pro Ser Arg Gly Asp Asp Gln Cys Gln Arg Gln Leu Gln Arg Ala Asn
            20                  25                  30

Leu Arg Pro Cys Glu Glu His Ile Arg Gln Arg Val Glu Gln Glu Gln
        35                  40                  45

Glu Gln Glu Gln Asp Glu Tyr Pro Tyr Ser Gln Arg Gly Ser Arg Gly
    50                  55                  60

Arg Arg Pro Gly Glu Ser Asp Glu Asp Gln Glu Gln Arg Cys Cys Asn
65                  70                  75                  80

Glu Leu Asn Arg Phe Gln Asn Asn Gln Arg Cys Met Cys Gln Ala Leu
                85                  90                  95

Gln Gln Ile Leu Gln Asn Gln Ser Phe Arg Phe Gln Asp Arg Ser
        100                 105                 110

Gln Leu His Gln Asn Gly Glu Gly Ala Gln Glu Leu Ala Pro Glu Leu
            115                 120                 125

Arg Val Gln Val Thr Lys Pro Leu Arg Pro
    130                 135

<210> SEQ ID NO 4
<211> LENGTH: 151
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: SEQ ID NO 4 (expressed sequence without signal
      sequence of Ara h 2.0201)

<400> SEQUENCE: 4

```
Arg Gln Gln Trp Glu Leu Gln Gly Asp Arg Cys Gln Ser Gln Leu
1               5                   10                  15

Glu Arg Ala Asn Leu Arg Pro Cys Glu Gln His Leu Met Gln Lys Ile
            20                  25                  30

Gln Arg Asp Glu Asp Ser Tyr Gly Arg Asp Pro Tyr Ser Pro Ser Gln
            35                  40                  45

Asp Pro Tyr Ser Pro Ser Gln Asp Pro Asp Arg Arg Asp Pro Tyr Ser
50                  55                  60

Pro Ser Pro Tyr Asp Arg Arg Gly Ala Gly Ser Ser Gln His Gln Glu
65                  70                  75                  80

Arg Cys Cys Asn Glu Leu Asn Glu Phe Glu Asn Asn Gln Arg Cys Met
                85                  90                  95

Cys Glu Ala Leu Gln Gln Ile Met Glu Asn Gln Ser Asp Arg Leu Gln
                100                 105                 110

Gly Arg Gln Gln Glu Gln Gln Phe Lys Arg Glu Leu Arg Asn Leu Pro
            115                 120                 125

Gln Gln Cys Gly Leu Arg Ala Pro Gln Arg Cys Asp Leu Glu Val Glu
        130                 135                 140

Ser Gly Gly Arg Asp Arg Tyr
145                 150

<210> SEQ ID NO 5
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: SEQ ID NO 5 (expressed sequence without signal
      sequence of Ara h 6.0101)

<400> SEQUENCE: 5

Met Arg Arg Glu Arg Gly Arg Gln Gly Asp Ser Ser Ser Cys Glu Arg
1               5                   10                  15

Gln Val Asp Arg Val Asn Leu Lys Pro Cys Glu Gln His Ile Met Gln
            20                  25                  30

Arg Ile Met Gly Glu Gln Glu Gln Tyr Asp Ser Tyr Asp Ile Arg Ser
            35                  40                  45

Thr Arg Ser Ser Asp Gln Gln Gln Arg Cys Cys Asp Glu Leu Asn Glu
50                  55                  60

Met Glu Asn Thr Gln Arg Cys Met Cys Glu Ala Leu Gln Gln Ile Met
65                  70                  75                  80

Glu Asn Gln Cys Asp Arg Leu Gln Asp Arg Gln Met Val Gln Gln Phe
                85                  90                  95

Lys Arg Glu Leu Met Asn Leu Pro Gln Gln Cys Asn Phe Arg Ala Pro
                100                 105                 110

Gln Arg Cys Asp Leu Asp Val Ser Gly Gly Arg Cys
            115                 120

<210> SEQ ID NO 6
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: SEQ ID NO 6 (C-terminus of Ara h 7 isotype
```

```
                                  7.0201)

<400> SEQUENCE: 6

His Gln Met Glu Arg Glu Leu Arg Asn Leu Pro Gln Asn Cys Gly Phe
1               5                   10                  15

Arg Ser Pro Ser Arg Cys Asp Leu Ser Ser Arg Thr Pro Tyr
            20                  25                  30

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: SEQ ID NO 7 (C-terminus of Ara h 7 isotype
      7.0201)

<400> SEQUENCE: 7

Asn Cys Gly Phe Arg Ser Pro Ser Arg Cys
1               5                   10

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: SEQ ID NO 8 (reactive epitope from C-terminus
      of Ara h 7 isotype 7.0201)

<400> SEQUENCE: 8

Gly Phe Arg Ser Pro Ser
1               5

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: SEQ ID NO 9 (C-terminus of Ara h 7 isotype
      7.0201)

<400> SEQUENCE: 9

Cys Gly Phe Arg Ser Pro Ser Arg Cys Asp
1               5                   10

<210> SEQ ID NO 10
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: SEQ ID NO 10 (C-terminus of Ara h 7 isotype
      7.0201)

<400> SEQUENCE: 10

Gln Asn Cys Gly Phe Arg Ser Pro Ser Arg Cys Asp Leu
1               5                   10
```

<210> SEQ ID NO 11
<211> LENGTH: 159
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: SEQ ID NO 11 (Ara h 7 isotype 7.0101, as
      expressed in example 1)

<400> SEQUENCE: 11

Met Ser His His His His His His His Leu Glu Val Leu Phe Gln
1               5                   10                  15

Gly Pro Ser Met Thr Arg Trp Asp Pro Asp Arg Gly Ser Arg Gly Ser
            20                  25                  30

Arg Trp Asp Ala Pro Ser Arg Gly Asp Asp Gln Cys Gln Arg Gln Leu
        35                  40                  45

Gln Arg Ala Asn Leu Arg Pro Cys Glu Glu His Met Arg Arg Val
    50                  55                  60

Glu Gln Glu Gln Glu Gln Gln Asp Glu Tyr Pro Tyr Ser Arg Arg
65                  70                  75                  80

Gly Ser Arg Gly Arg Gln Pro Gly Glu Ser Asp Glu Asn Gln Glu Gln
                85                  90                  95

Arg Cys Cys Asn Glu Leu Asn Arg Phe Gln Asn Asn Gln Arg Cys Met
            100                 105                 110

Cys Gln Ala Leu Gln Gln Ile Leu Gln Asn Gln Ser Phe Trp Val Pro
        115                 120                 125

Ala Gly Gln Glu Pro Val Ala Ser Asp Gly Glu Gly Ala Gln Glu Leu
    130                 135                 140

Ala Pro Glu Leu Arg Val Gln Val Thr Lys Pro Leu Arg Pro Leu
145                 150                 155

<210> SEQ ID NO 12
<211> LENGTH: 164
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: SEQ ID NO 12 (Ara h 7 isotype 7.0201, as
      expressed in example 1)

<400> SEQUENCE: 12

Met Ser His His His His His His His Leu Glu Val Leu Phe Gln
1               5                   10                  15

Gly Pro Ser Met Thr Arg Trp Asp Pro Asp Arg Gly Ser Arg Gly Ser
            20                  25                  30

Arg Trp Asp Ala Pro Ser Arg Gly Asp Asp Gln Cys Gln Arg Gln Leu
        35                  40                  45

Gln Arg Ala Asn Leu Arg Pro Cys Glu Glu His Ile Arg Gln Arg Val
    50                  55                  60

Glu Lys Glu Gln Glu Gln Glu Gln Asp Glu Tyr Pro Tyr Ile Gln Arg
65                  70                  75                  80

Gly Ser Arg Gly Gln Arg Pro Gly Glu Ser Asp Glu Asp Gln Glu Gln
                85                  90                  95

Arg Cys Cys Asn Glu Leu Asn Arg Phe Gln Asn Asn Gln Arg Cys Met
            100                 105                 110

Cys Gln Ala Leu Gln Gln Ile Leu Gln Asn Gln Ser Phe Arg Phe Gln

```
                115                 120                 125

Gln Asp Arg Ser Gln Leu His Gln Met Glu Arg Glu Leu Arg Asn Leu
        130                 135                 140

Pro Gln Asn Cys Gly Phe Arg Ser Pro Ser Arg Cys Asp Leu Ser Ser
145                 150                 155                 160

Arg Thr Pro Tyr

<210> SEQ ID NO 13
<211> LENGTH: 158
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: SEQ ID NO 13 (Ara h 7 isotype 7.0, as expressed
      in example 1)

<400> SEQUENCE: 13

Met Ser His His His His His His His Leu Glu Val Leu Phe Gln
1               5                   10                  15

Gly Pro Ser Met Thr Arg Trp Asp Pro Asp Arg Gly Ser Arg Gly Leu
            20                  25                  30

Arg Trp Asp Ala Pro Ser Arg Gly Asp Asp Gln Cys Gln Arg Gln Leu
        35                  40                  45

Gln Arg Ala Asn Leu Arg Pro Cys Glu Glu His Ile Arg Gln Arg Val
    50                  55                  60

Glu Gln Glu Gln Glu Gln Gln Asp Glu Tyr Pro Tyr Ser Gln Arg
65                  70                  75                  80

Gly Ser Arg Gly Arg Arg Pro Gly Glu Ser Asp Glu Asp Gln Glu Gln
                85                  90                  95

Arg Cys Cys Asn Glu Leu Asn Arg Phe Gln Asn Asn Gln Arg Cys Met
            100                 105                 110

Cys Gln Ala Leu Gln Gln Ile Leu Gln Asn Gln Ser Phe Arg Phe Gln
        115                 120                 125

Gln Asp Arg Ser Gln Leu His Gln Asn Gly Glu Gly Ala Gln Glu Leu
    130                 135                 140

Ala Pro Glu Leu Arg Val Gln Val Thr Lys Pro Leu Arg Pro
145                 150                 155

<210> SEQ ID NO 14
<211> LENGTH: 165
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: SEQ ID NO 14 (Ara h 2 isotype 2.0201, as
      expressed in example 1)

<400> SEQUENCE: 14

Met Ser His His His His His His Ile Glu Gly Arg Thr Met Arg Gln
1               5                   10                  15

Gln Trp Glu Leu Gln Gly Asp Arg Arg Cys Gln Ser Gln Leu Glu Arg
            20                  25                  30

Ala Asn Leu Arg Pro Cys Glu Gln His Leu Met Gln Lys Ile Gln Arg
        35                  40                  45

Asp Glu Asp Ser Tyr Gly Arg Asp Pro Tyr Ser Pro Ser Gln Asp Pro
    50                  55                  60
```

Tyr Ser Pro Ser Gln Asp Pro Asp Arg Arg Asp Pro Tyr Ser Pro Ser
65                  70                  75                  80

Pro Tyr Asp Arg Arg Gly Ala Gly Ser Ser Gln His Gln Glu Arg Cys
                85                  90                  95

Cys Asn Glu Leu Asn Glu Phe Glu Asn Asn Gln Arg Cys Met Cys Glu
            100                 105                 110

Ala Leu Gln Gln Ile Met Glu Asn Gln Ser Asp Arg Leu Gln Gly Arg
        115                 120                 125

Gln Gln Glu Gln Gln Phe Lys Arg Glu Leu Arg Asn Leu Pro Gln Gln
    130                 135                 140

Cys Gly Leu Arg Ala Pro Gln Arg Cys Asp Leu Glu Val Glu Ser Gly
145                 150                 155                 160

Gly Arg Asp Arg Tyr
                165

<210> SEQ ID NO 15
<211> LENGTH: 143
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: SEQ ID NO 15 (Ara h 6 isotype 6.0101, as
      expressed in example 1)

<400> SEQUENCE: 15

Met Ser His His His His His His Leu Glu Val Leu Phe Gln
1               5                   10                  15

Gly Pro Ser Met Arg Arg Glu Arg Gly Arg Gln Gly Asp Ser Ser Ser
                20                  25                  30

Cys Glu Arg Gln Val Asp Arg Val Asn Leu Lys Pro Cys Glu Gln His
            35                  40                  45

Ile Met Gln Arg Ile Met Gly Glu Gln Glu Gln Tyr Asp Ser Tyr Asp
        50                  55                  60

Ile Arg Ser Thr Arg Ser Ser Asp Gln Gln Gln Arg Cys Cys Asp Glu
65                  70                  75                  80

Leu Asn Glu Met Glu Asn Thr Gln Arg Cys Met Cys Glu Ala Leu Gln
                85                  90                  95

Gln Ile Met Glu Asn Gln Cys Asp Arg Leu Gln Asp Arg Gln Met Val
            100                 105                 110

Gln Gln Phe Lys Arg Glu Leu Met Asn Leu Pro Gln Gln Cys Asn Phe
        115                 120                 125

Arg Ala Pro Gln Arg Cys Asp Leu Asp Val Ser Gly Gly Arg Cys
    130                 135                 140

<210> SEQ ID NO 16
<211> LENGTH: 615
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: SEQ ID NO 16 Ara h 1.01.01 as used in example 3

<400> SEQUENCE: 16

Met Ser His His His His His His Ile Glu Gly Arg Thr Met Lys Ser
1               5                   10                  15

```
Ser Pro Tyr Gln Lys Lys Thr Glu Asn Pro Cys Ala Gln Arg Cys Leu
            20                  25                  30

Gln Ser Cys Gln Gln Glu Pro Asp Asp Leu Lys Gln Lys Ala Cys Glu
        35                  40                  45

Ser Arg Cys Thr Lys Leu Glu Tyr Asp Pro Arg Cys Val Tyr Asp Pro
    50                  55                  60

Arg Gly His Thr Gly Thr Thr Asn Gln Arg Ser Pro Pro Gly Glu Arg
65                  70                  75                  80

Thr Arg Gly Arg Gln Pro Gly Asp Tyr Asp Asp Arg Arg Gln Pro
                85                  90                  95

Arg Arg Glu Glu Gly Gly Arg Trp Gly Pro Ala Gly Pro Arg Glu Arg
                100                 105                 110

Glu Arg Glu Glu Asp Trp Arg Gln Pro Arg Glu Asp Trp Arg Arg Pro
            115                 120                 125

Ser His Gln Gln Pro Arg Lys Ile Arg Pro Glu Gly Arg Glu Gly Glu
        130                 135                 140

Gln Glu Trp Gly Thr Pro Gly Ser His Val Arg Glu Glu Thr Ser Arg
145                 150                 155                 160

Asn Asn Pro Phe Tyr Phe Pro Ser Arg Arg Phe Ser Thr Arg Tyr Gly
                165                 170                 175

Asn Gln Asn Gly Arg Ile Arg Val Leu Gln Arg Phe Asp Gln Arg Ser
                180                 185                 190

Arg Gln Phe Gln Asn Leu Gln Asn His Arg Ile Val Gln Ile Glu Ala
            195                 200                 205

Lys Pro Asn Thr Leu Val Leu Pro Lys His Ala Asp Ala Asp Asn Ile
    210                 215                 220

Leu Val Ile Gln Gln Gly Gln Ala Thr Val Thr Val Ala Asn Gly Asn
225                 230                 235                 240

Asn Arg Lys Ser Phe Asn Leu Asp Glu Gly His Ala Leu Arg Ile Pro
                245                 250                 255

Ser Gly Phe Ile Ser Tyr Ile Leu Asn Arg His Asp Asn Gln Asn Leu
                260                 265                 270

Arg Val Ala Lys Ile Ser Met Pro Val Asn Thr Pro Gly Gln Phe Glu
            275                 280                 285

Asp Phe Phe Pro Ala Ser Ser Arg Asp Gln Ser Ser Tyr Leu Gln Gly
    290                 295                 300

Phe Ser Arg Asn Thr Leu Glu Ala Ala Phe Asn Ala Glu Phe Asn Glu
305                 310                 315                 320

Ile Arg Arg Val Leu Leu Glu Glu Asn Ala Gly Gly Glu Gln Glu Glu
                325                 330                 335

Arg Gly Gln Arg Arg Trp Ser Thr Arg Ser Ser Glu Asn Asn Glu Gly
                340                 345                 350

Val Ile Val Lys Val Ser Lys Glu His Val Glu Glu Leu Thr Lys His
            355                 360                 365

Ala Lys Ser Val Ser Lys Lys Gly Ser Glu Glu Glu Gly Asp Ile Thr
    370                 375                 380

Asn Pro Ile Asn Leu Arg Glu Gly Glu Pro Asp Leu Ser Asn Asn Phe
385                 390                 395                 400

Gly Lys Leu Phe Glu Val Lys Pro Asp Lys Lys Asn Pro Gln Leu Gln
                405                 410                 415

Asp Leu Asp Met Met Leu Thr Cys Val Glu Ile Lys Glu Gly Ala Leu
            420                 425                 430

Met Leu Pro His Phe Asn Ser Lys Ala Met Val Ile Val Val Val Asn
```

```
            435                 440                 445
Lys Gly Thr Gly Asn Leu Glu Leu Val Ala Val Arg Lys Glu Gln Gln
    450                 455                 460

Gln Arg Gly Arg Glu Glu Glu Asp Glu Asp Glu Glu Glu Glu
465                 470                 475                 480

Gly Ser Asn Arg Glu Val Arg Arg Tyr Thr Ala Arg Leu Lys Glu Gly
                485                 490                 495

Asp Val Phe Ile Met Pro Ala Ala His Pro Val Ala Ile Asn Ala Ser
                500                 505                 510

Ser Glu Leu His Leu Leu Gly Phe Gly Ile Asn Ala Glu Asn His
            515                 520                 525

Arg Ile Phe Leu Ala Gly Asp Lys Asp Asn Val Ile Asp Gln Ile Glu
            530                 535                 540

Lys Gln Ala Lys Asp Leu Ala Phe Pro Gly Ser Gly Glu Gln Val Glu
545                 550                 555                 560

Lys Leu Ile Lys Asn Gln Lys Glu Ser His Phe Val Ser Ala Arg Pro
                565                 570                 575

Gln Ser Gln Ser Gln Ser Pro Ser Ser Pro Glu Lys Glu Ser Pro Glu
            580                 585                 590

Lys Glu Asp Gln Glu Glu Asn Gln Gly Gly Lys Gly Pro Leu Leu
            595                 600                 605

Ser Ile Leu Lys Ala Phe Asn
    610                 615

<210> SEQ ID NO 17
<211> LENGTH: 527
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: SEQ ID NO 17 Ara h 3.01.01 as used in example 3

<400> SEQUENCE: 17

Met Ser His His His His His His His Leu Glu Val Leu Phe Gln
1               5                   10                  15

Gly Pro Ser Met Arg Gln Gln Pro Glu Glu Asn Ala Cys Gln Phe Gln
                20                  25                  30

Arg Leu Asn Ala Gln Arg Pro Asp Asn Arg Ile Glu Ser Glu Gly Gly
            35                  40                  45

Tyr Ile Glu Thr Trp Asn Pro Asn Asn Gln Glu Phe Glu Cys Ala Gly
    50                  55                  60

Val Ala Leu Ser Arg Leu Val Leu Arg Arg Asn Ala Leu Arg Arg Pro
65                  70                  75                  80

Phe Tyr Ser Asn Ala Pro Gln Glu Ile Phe Ile Gln Gln Gly Arg Gly
                85                  90                  95

Tyr Phe Gly Leu Ile Phe Pro Gly Cys Pro Arg His Tyr Glu Glu Pro
            100                 105                 110

His Thr Gln Gly Arg Arg Ser Gln Ser Gln Arg Pro Pro Arg Arg Leu
        115                 120                 125

Gln Gly Glu Asp Gln Ser Gln Gln Arg Asp Ser His Gln Lys Val
    130                 135                 140

His Arg Phe Asp Glu Gly Asp Leu Ile Ala Val Pro Thr Gly Val Ala
145                 150                 155                 160

Phe Trp Leu Tyr Asn Asp His Asp Thr Asp Val Val Ala Val Ser Leu
```

```
                    165                 170                 175
Thr Asp Thr Asn Asn Asp Asn Gln Leu Asp Gln Phe Pro Arg Arg
            180                 185                 190

Phe Asn Leu Ala Gly Asn Thr Glu Gln Glu Phe Leu Arg Tyr Gln Gln
        195                 200                 205

Gln Ser Arg Gln Ser Arg Arg Ser Leu Pro Tyr Ser Pro Tyr Ser
    210                 215                 220

Pro Gln Ser Gln Pro Arg Gln Glu Glu Arg Glu Phe Ser Pro Arg Gly
225                 230                 235                 240

Gln His Ser Arg Arg Glu Arg Ala Gly Gln Glu Glu Asn Glu Gly
                245                 250                 255

Gly Asn Ile Phe Ser Gly Phe Thr Pro Glu Phe Leu Glu Gln Ala Phe
            260                 265                 270

Gln Val Asp Asp Arg Gln Ile Val Gln Asn Leu Arg Gly Glu Thr Glu
        275                 280                 285

Ser Glu Glu Glu Gly Ala Ile Val Thr Val Arg Gly Gly Leu Arg Ile
    290                 295                 300

Leu Ser Pro Asp Arg Lys Arg Ala Asp Glu Glu Glu Tyr Asp
305                 310                 315                 320

Glu Asp Glu Tyr Glu Tyr Asp Glu Glu Asp Arg Arg Arg Gly Arg Gly
                325                 330                 335

Ser Arg Gly Arg Gly Asn Gly Ile Glu Glu Thr Ile Cys Thr Ala Ser
            340                 345                 350

Ala Lys Lys Asn Ile Gly Arg Asn Arg Ser Pro Asp Ile Tyr Asn Pro
        355                 360                 365

Gln Ala Gly Ser Leu Lys Thr Ala Asn Asp Leu Asn Leu Ile Leu
    370                 375                 380

Arg Trp Leu Gly Pro Ser Ala Glu Tyr Gly Asn Leu Tyr Arg Asn Ala
385                 390                 395                 400

Leu Phe Val Ala His Tyr Asn Thr Asn Ala His Ser Ile Ile Tyr Arg
                405                 410                 415

Leu Arg Gly Arg Ala His Val Gln Val Val Asp Ser Asn Gly Asn Arg
            420                 425                 430

Val Tyr Asp Glu Glu Leu Gln Glu Gly His Val Leu Val Val Pro Gln
        435                 440                 445

Asn Phe Ala Val Ala Gly Lys Ser Gln Ser Glu Asn Phe Glu Tyr Val
    450                 455                 460

Ala Phe Lys Thr Asp Ser Arg Pro Ser Ile Ala Asn Leu Ala Gly Glu
465                 470                 475                 480

Asn Ser Val Ile Asp Asn Leu Pro Glu Glu Val Val Ala Asn Ser Tyr
                485                 490                 495

Gly Leu Gln Arg Glu Gln Ala Arg Gln Leu Lys Asn Asn Asn Pro Phe
            500                 505                 510

Lys Phe Phe Val Pro Pro Ser Gln Gln Ser Pro Arg Ala Val Ala
        515                 520                 525
```

ASSAY FOR THE DIAGNOSIS OF PEANUT ALLERGY

The instant application contains a Sequence Listing which has been filed electronically in ASCII format and is hereby incorporated by reference in its entirety. Said ASCII copy, created on Jan. 16, 2018, is named 000254US_SL.txt and is 27,243 bytes in size.

The present invention relates to a diagnostically useful carrier comprising a means for specifically capturing an antibody to Ara h 7 isotype 7.0201 in a sample from a subject; a method comprising the step detecting in a sample from a subject the presence or absence of an antibody to Ara h 7 isotype 7.0201 and a pharmaceutical composition comprising Ara h 7 isotype 7.0201 or a variant thereof.

Among food allergies, those relating to peanut (*Arachis hypogea*) have attracted the most research attention because they are relatively common, typically permanent, and often severe. Food anaphylaxis fatality registries in the United States implicate peanut as a trigger in 59% of 63 deaths and indicate that adolescents and young adults are at greatest risk, with additional risk factors being asthma and delayed injection of epinephrine during anaphylaxis. Peanut is a ubiquitous food, and affected patients, who often react to small doses, are faced with numerous hurdles to avoid ingestion and experience a negative effect on quality of life.

Peanut allergy is primarily suspected in two circumstances: when a patient demonstrates severe allergic reactions or in the context of monitoring allergic conditions to other foods or aeroallergens. When peanut sensitization is discovered by a positive skin prick-test (SPT), or peanut-specific IgE assays, the diagnostic reliability of which relative to clinical disease is currently insufficient, the patient is referred to a specialized center that provides a diagnosis based on a double-blind placebo-controlled food challenge (DBPCFC). This procedure is the gold standard for food allergy diagnosis, but its application requires hospitalization and is costly. Furthermore, even under the control of trained physicians, DBPCFC with peanut may cause severe or even life-threatening reactions.

Therefore, there is a great deal of interest in improved assays for the diagnosis of peanut allergies based on the detection of specific antibodies in samples from subjects suspected of suffering from a peanut allergy.

Assays described in the state of the art rely on the detection of major peanut allergens such as Ara h 1, Ara h 2, Ara h 3 and Ara h 6 using natural or recombinant allergens (Flinterman, A. E., van Hoffen, E., den Hartog, Jager C. F., Koppelman, S., Pasmans, S. G., Hoekstra, M. O., Bruijnzeel-Koomen, C. A., Knulst, A. C., Knol, E. F. (2007): Children with peanut allergy recognize predominantly Ara h 2 and Ara h 6, which remains stable over time, Clin Exp Allergy 2007; 37; 1221-1228; de Leon, M. P., Drew, A. C., Glaspole, I. N., Suphioglu, C., O'Hehir, R. E., Rolland, J. M. (2007): IgE cross-reactivity between the major peanut allergen Ara h 2 and tree nut allergens, Mol Immunol 2007; 44: 463-471).

Ara h 2 and Ara h 6 are 2S storage proteins of the conglutin type and belong to the prolamin superfamily. Members of this family are characterized by the presence of a conserved pattern of six or eight cysteine residues located within a sequence of about 100 amino acid residues forming three or four intramolecular disulfide bonds. They are stable to thermal processing and proteolysis.

Ara h 2 is a major allergen of peanuts and occurs in two isoforms with different molecular weights (MWs), which is due to a 12-amino-acid insert with a MW of 1,414 Da. In its primary protein sequence, Ara h 6 exhibits an identity with Ara h 2 of 53% and, in comparison with Ara h 2, possesses ten instead of eight cysteines but no N-glycosylation site. Like Ara h 2, Ara h 6 is resistant to digestion and stable against heating, especially in baking processes. The tertiary structure of Ara h 6 was elucidated and at least four α-helical structures and the location parameters of disulfide bonds were identified. In digestion experiments under physiological conditions, Ara h 2 and Ara h 6 form stable fragments even under reducing conditions. This supports the idea that cross-reactivities between Ara h 2 and Ara h 6 are mediated by IgE reactive conformational epitopes (Schmidt, H., Krause, S., Gelhaus, C., Petersen, A., Janssen, O., and Becker, W. M. (2010): Detection and structural characterization of natural Ara h 7, the third peanut allergen of the 2S albumin family, J Proteome Res 2010; 9: 3701-709).

Ara h 7 is another peanut allergen, and its isotype Ara h 7.0101 was at first identified by the phage display system and cloned, but initially the natural counterpart was not found in peanut extract, which is one of the reasons why its impact on allergy is described in the state of the art as low.

Schmidt et al. (2010, Detection and Structural Characterization of Natural Ara h 7, the Third Peanut Allgergen of the 2S Albumin Family) found that another isotype exists (Ara h 7.0201) Ara h 7.0 is another isotype published in the data base UNIPROT in addition to 7.0101). However, the Schmidt et al. do not mention diagnostic applications; theirs is a purely proteomic study.

What is more, only five out of six patients' sera used by Schmidt et al., which had been preselected by Ara h 7.0101 reactivity, showed positive IgE binding with Ara h 7.0201, suggesting that the latter is in fact less (!) reactive and therefore of even lower diagnostic value than Ara h 7.0101. Therefore, Ara h 7.0201 has not been used for routine diagnostics until now as far as the inventors are aware.

In addition, several studies have evaluated a range of immunologic parameters using purified peanut proteins (Ara h 1-3, Ara h 6) and found a correlation of clinical severity with recognition of Ara h 2 and 6 at low concentrations, and Ara h 1 and 3 at higher concentrations, indicating apparent increased potency of Ara h 2 (Peeters, K. A., Koppelman, S. J., van Hoffen, E., van der Tas, C. W., den Hartog, Jager C. F., Penninks, A. H., Hefle, S. L., Bruijnzeel-Koomen, C. A., Knol, E. F., and Knulst, A. C. (2007): Does skin prick test reactivity to purified allergens correlate with clinical severity of peanut allergy? Clin Exp Allergy. 2007 January; 37(1):108-15.).

The IgE antibody reactivity to peanut allergens Ara h 1, Ara h 2, Ara h 3, Ara h 6 and Ara h 7 has been investigated in peanut-allergic patients using recombinant allergens as well. Codreanu et al. evaluated the performance of the proteins in the diagnosis of peanut allergy in 2 large cohorts of peanut-allergic patients. Measurements of specific IgE were performed using a UniCAP platform with Immuno-CAP tests. They reported that Ara h 2 is the allergen to which peanut-allergic patients are most frequently sensitized, with detectable IgE antibodies being present in 77-100% of cases, followed by Ara h 6 (38-80% cases). By contrast, their data suggest that no patients are monosensitive to Ara h 7 (Codreanu, F., Collignon, O., Roitel, O., Thouvenot. B., Sauvage, C., Vilain, A. C., Cousin, M. O., Decoster, A., Renaudin, J M., Astier, C., Monnez, J M., Vallois, P., Morisset, M., Moneret-Vautrin, D. A., Brulliard, M., Ogier, V., Castelain, M. C., Kanny, G., Bihain, B. E., and Jacquenet. S. (2011): A novel immunoassay using recombinant allergens simplifies peanut allergy diagnosis, Int Arch Allergy Immunol, 2011; 154(3):216-26.). The findings that no patients are monosensitive to Ara h 7 has been another reason not to use any isotype of Ara h 7 for routine diagnostics, since it was believed that it does not increase the sensitivity of diagnostic tests for identifying peanut-allergic patients.

At present, a number of patients allergic to peanuts cannot be diagnosed as allergic based on the results of conventional tests. Not in the least in view of the severity of the symptoms associated with peanut allergy, there is continuously increasing demand for diagnostics having the utmost degree of sensitivity.

The problem underlying the present invention is to overcome any shortcomings associated with state of the art diagnostic assays based on the detection of antibodies to peanut allergens.

Another problem underlying the present invention is to provide a new antigen, a new assay, new reagents and a new method that allows for the diagnosis of allergy in patients that would be un- or misdiagnosed using conventional assay systems.

Another problem underlying the present invention is to provide an improved antigen for the detection of IgE antibodies in patients suffering from nut allergies, preferably peanut allergies.

Another problem underlying the present invention is to provide an alternative method and alternative reagents for diagnosing nut allergies, preferably peanut allergies.

Another problem underlying the present invention is to provide a method and reagents that, when used in combination with known methods and reagents for the diagnosis of nut allergies, preferably peanut allergies, increase the overall diagnostic reliability, in particular sensitivity.

Another problem underlying the present invention is to provide a method and reagents that, with minimal investment in resources, in particular time and the number of antigens used, allows for the diagnosis of nut allergies, preferably peanut allergies, with the maximum overall diagnostic reliability, in particular sensitivity.

The problem underlying the present invention is solved by the subject-matter of the attached independent and dependent claims.

In a first aspect, the problem underlying the present invention is solved by a diagnostically useful carrier comprising a means for specifically capturing an antibody to Ara h 7 isotype 7.0201, preferably SEQ ID NO6, more preferably to a sequence from the group comprising SEQ ID NO7, SEQ ID NO8, SEQ ID NO9 and SEQ ID NO10, most preferably to SEQ ID NO8, in a sample from a subject.

In another preferred embodiment of the first aspect, the carrier further comprises a means for specifically capturing an antibody to one or more further antigens from the group comprising Ara h 2, Ara h 6, Ara h 1. Ara h 3, Ara h 9, Ara h 8 and Ara h 5, more preferably from the group comprising Ara h 2, Ara h 6, Ara h 1, Ara h 3, Ara h 9, most preferably an antibody to Ara h 2 and/or an antibody to Ara h 6.

In another preferred embodiment of the first aspect, the diagnostically useful carrier is selected from the group comprising a bead, a test strip, a microtiter plate, a microarray, a solid polymer derived from cellulose, a blot, preferably from the group comprising western blot, line blot and dot blot, a glass surface, a biochip and a membrane, and is most preferably a microtiter plate or a line blot.

In a second aspect, the problem underlying the present invention is solved by a kit comprising a diagnostically useful carrier comprising a means for specifically capturing an antibody to antigen Ara h 7 isotype 7.0201, preferably SEQ ID NO6 in a sample from a subject, preferably further comprising a means for specifically capturing an antibody to one or more further antigens, more preferably from the group Ara h 2, Ara h 6, Ara h 1, Ara h 3, Ara h 9, Ara h 8 and Ara h 5, more preferably from the group comprising Ara h 2, Ara h 6, Ara h 1, Ara h 3, Ara h 9, most preferably an antibody to Ara h 2 and/or an antibody to Ara h 6, optionally as well as a means for specifically detecting a captured antibody.

In another preferred embodiment of the second aspect, the diagnostically useful carrier further comprises a means for specifically capturing an antibody to one or more further antigens from the group comprising Ara h 2, Ara h 6, Ara h 1, Ara h 3, Ara h 9, Ara h 8 and Ara h 5, wherein the means for specifically capturing an antibody to Ara h 7 isotype 7.0201, preferably SEQ ID NO6, more preferably to a sequence from the group comprising SEQ ID NO7, SEQ ID NO8, SEQ ID NO9 and SEQ ID NO10, most preferably to SEQ ID NO8, and the means for specifically capturing an antibody to one or more further antigens are on separate carriers.

In a preferred embodiment of the second aspect, the diagnostically useful carrier further comprises a means for specifically capturing an antibody to one or more further antigens from the group comprising Ara h 2, Ara h 6, Ara h 1, Ara h 3, Ara h 9, Ara h 8 and Ara h 5, wherein the means for specifically capturing an antibody to Ara h 7 isotype 7.0201, preferably SEQ ID NO6 more preferably to a sequence from the group comprising SEQ ID NO7, SEQ ID NO8, SEQ ID NO9 and SEQ ID NO10, most preferably to SEQ ID NO8, and the means for specifically capturing an antibody to one or more further antigens are on one carrier, preferably covalently linked to one carrier.

In a third aspect, the problem underlying the present invention is solved by a method, preferably for diagnosing or aiding the diagnosis of a nut allergy, more preferably a peanut allergy, comprising the step detecting in a sample from a subject the presence of an antibody to Ara h 7 isotype 7.0201, preferably SEQ ID NO6, more preferably to a sequence from the group comprising SEQ ID NO7, SEQ ID NONO8, SEQ ID NO9 and SEQ ID NO10, most preferably to SEQ ID NO8.

In a preferred embodiment of the third aspect, the method further comprises detecting in a sample from a subject the presence of an antibody to one or more further antigens, preferably selected from the group comprising Ara h 2, Ara h 6, Ara h 1, Ara h 3, Ara h 9, Ara h 8 and Ara h 5, more preferably from the group comprising Ara h 2, Ara h 6, Ara h 1, Ara h 3 and Ara h 9, most preferably Ara h 2 and/or Ara h 6.

In another preferred embodiment of the third aspect, the presence of an antibody to Ara h 7 isotype 7.0201, preferably SEQ ID NO6 more preferably to a sequence from the group comprising SEQ ID NO7, SEQ ID NONO8, SEQ ID NO9 and SEQ ID NO10, most preferably to SEQ ID NO8 and the presence of an antibody to one or more further antigens, preferably Ara h 2 and/or Ara h 6, is detected simultaneously.

In another preferred embodiment of the third aspect, the presence of an antibody to Ara h 7 isotype 7.0201, preferably SEQ ID NO6, more preferably to a sequence from the group comprising SEQ ID NO7, SEQ ID NONO8, SEQ ID NO9 and SEQ ID NO10, most preferably to SEQ ID NO8, and the presence of an antibody to one or more further antigens, preferably Ara h 6 and/or Ara h 2, is detected in spatially separate binding reactions.

In another preferred embodiment of the third aspect, the presence of an antibody to Ara h 7 isotype 7.0201, and the presence of an antibody to one or more further antigens, preferably Ara h 6 and/or Ara h 2, is detected in a one-pot reaction.

In another preferred embodiment of the third aspect, the method comprises the step contacting the diagnostically useful carrier according to the present invention with a sample from the subject.

In another preferred embodiment of any aspect, the subject suffers from or is suspected to suffer from an allergy, preferably an allergy to a nut, more preferably a peanut.

In another preferred embodiment of any aspect, the antibody to Ara h 7 isotype 7.0201, preferably SEQ ID NO6 is an antibody monospecific to Ara h 7 isotype 7.0201, more preferably to a sequence from the group comprising SEQ ID NO7, SEQ ID NONO8, SEQ ID NO9 and SEQ ID NO10, most preferably to SEQ ID NO8.

In a fourth aspect, the problem underlying the present invention is solved by a pharmaceutical composition comprising SEQ ID NO 8, more preferably a sequence from the group comprising SEQ ID NO6, SEQ ID NO7, SEQ ID NO8, SEQ ID NO9 and SEQ ID NO10, more preferably SEQ ID NO6, most preferably Ara h 7 isotype 7.0201 or a variant thereof and preferably one or more further antigens from the group comprising Ara h 2, Ara h 6, Ara h 1, Ara h 3, Ara h 9, Ara h 8 and Ara h 5 and a variant thereof, more preferably from the group comprising Ara h 2, Ara h 6, Ara h 1, Ara h 3, Ara h 9 and a variant thereof, most preferably Ara h 2 and/or Ara h 6.

In a fifth aspect, the problem underlying the present invention is solved by a polypeptide comprising SEQ ID NO 8, more preferably a sequence from the group comprising SEQ ID NO6, SEQ ID NO7, SEQ ID NO8, SEQ ID NO9 and SEQ ID NO10, more preferably SEQ ID NO6, most preferably Ara h 7 isotype 7.0201, or a variant thereof.

In a preferred embodiment, the polypeptide according to the present invention is immobilized, purified, and/or a fusion protein, preferably purified, more preferably immobilized and purified, more preferably purified and recombinant and immobilized.

In a sixth aspect, the problem is solved by a use of the polypeptide, the carrier or the kit according to the present invention for the diagnosis of peanut allergy, wherein preferably the sensitivity is increased.

In a seventh aspect, the problem is solved by a use of the polypeptide according to the present invention for the manufacture of a kit for the diagnosis of peanut allergy, wherein preferably the sensitivity of the diagnosis is increased.

Preferably the polypeptide comprising SEQ ID NO 8, more preferably a sequence from the group comprising SEQ ID NO6, SEQ ID NO7, SEQ ID NO8, SEQ ID NO9 and SEQ ID NO10, more preferably SEQ ID NO6, most preferably Ara h 7 isotype 7.0201 or a variant thereof is a composition comprising said polypeptide and Ara h 2 and/or Ara h 6 or a variant thereof.

In an $8^{th}$ aspect, the problem is solved by an antibody, preferably IgE class antibody binding specifically to Ara h 7 isotype 7.0201, preferably SEQ ID NO6, more preferably a sequence from the group comprising SEQ ID NO7, SEQ ID NO8, SEQ ID NO9 and SEQ ID NO10, most preferably to SEQ ID NO8, which is preferably an isolated antibody. The antibody may be isolated by affinity chromatography using standard protocols from a patient sample using the antigen as affinity ligand.

In a $9^{th}$ aspect, the problem is solved by a use of the antibody according to the present invention for the diagnosis of peanut allergy or for the manufacture of a kit for the diagnosis of peanut allergy.

The present invention centers around the detection of an antibody to Ara h 7 isotype 7.0201, more specifically its surprisingly immunoreactive C-terminus, in particular the epitope comprising SEQ ID NO8, as part of a diagnostic method practiced on a sample from a patient suspected of having an allergy to a nut, more surprisingly some allergic patients have antibodies only that are monospecific to Ara h 7 isotype 7.0201 comprising SEQ ID NO8 and do not bind to the other Ara h 7 isotypes, more specifically 7.0101 and Ara h 7.0, let alone Ara h 2 or Ara h 6.

This is in striking contrast to previously published studies, for example the one by Codreanu et al., which suggest that the detection of an antibody to any (!) Ara h 7 isotype has limited diagnostic value compared to or, in particular, beyond data resulting from the detection of Ara h 2 and/or Ara h 6. In particular, these studies suggest that there are no patients having antibodies monospecific to any Ara h 7 isotype.

The invention relates to a diagnostically useful carrier, which is preferably a solid carrier for contacting a means for specifically capturing an antibody, which means is associated with said carrier, with a bodily fluid sample from a subject, preferably a mammalian subject, more preferably a human subject. In a preferred embodiment the solid carrier is a diagnostic device, more preferably selected from the group comprising a bead, a test strip, a microtiter plate, blot, a glass surface, a biochip and a membrane, more preferably from the group comprising a blot, a test strip and a membrane. In a most preferred embodiment, the diagnostically useful carrier is a microtiter plate or line blot (Raoult, D., and Dasch, G. A. (1989), The line blot: an immunoassay for monoclonal and other antibodies. Its application to the serotyping of gram-negative bacteria. J. Immunol. Methods, 125 (1-2), 57-65; WO2013041540). In a preferred embodiment, the term "line blot", as used herein refers to a test strip, more preferably membrane-based, that has been coated with one or more means for capturing an antibody, preferably a polypeptide each. If two or more means are used, they are preferably spatially separated on the carrier. Preferably, the width of the bands is at least 30, more preferably 40, 50, 60, 70 or 80% the width of the test strip. The test strip may comprise one or more control bands for confirming that it has been contacted with sample sufficiently long and under adequate conditions, in particular in the presence of human serum, antibody conjugate, or both. A multitude of line blots are commercially available, for example from EUROIMMUN, Lübeck, Germany.

The sample from a subject used to practice the present invention comprises antibodies, also referred to as immunoglobulins. Typically, the sample is a bodily fluid comprising a representative set of the entirety of the subject's immunoglobulins. However, the sample, once provided, may be subjected to further processing which may include fractionation, centrifugation, enriching or isolating the entirety of immunoglobulins or any immunoglobulin class of the subject, preferably IgE, which may affect the relative distribution of immunoglobulins of the various classes. The sample may be selected from the group comprising wholeblood, serum, cerebrospinal fluid and saliva and is preferably serum. In a most preferred embodiment, the sample comprises IgE class antibodies. In a more preferred embodiment, the sample comprises a representative set of the subject's antibodies from classes IgA, IgG and IgE, preferably IgG and IgE, more preferably IgG1, IgG4 and IgE, wherein, most preferably, the ratio of number of antibodies to different antigens is essentially unaltered compared to the ratio in the sample as obtained from the subject.

The diagnostically useful carrier comprises a means for specifically capturing an antibody to Ara h 7 isotype 7.0201, preferably to SEQ ID NO8, optionally in combination with one or more further antigens such as Ara h 2 and/or Ara h 6. In a preferred embodiment, the terms "Ara h 7 isotype 7.0201", "Ara h 2", "Ara h 6", "Ara h 1", "Ara h 3", "Ara h 5", "Ara h 8" and "Ara h 9", as used herein, refer to the polypeptides represented by data base codes B4XID4 (Ara h 7 Isotype 7.0201, expressed sequence without signal peptide: SEQ ID NO2) and, Q6PSU2 (Ara h 2, expressed sequence without signal peptide: SEQ ID NO4), Q647G9 (Ara h 6, expressed sequence without signal peptide: SEQ ID NO5), P43238 (Ara h 1), O82580 (Ara h 3), Q9SQI9 (Ara h 5), B0YIU5 or Q6VT83 (two isotypes of Ara h 8), and B6CG41 or B6CEX8 (two isotypes of Ara h 9) and variants thereof, respectively. Preferably the term "Ara h 7", as used herein, refers to the entirety of the three Ara h 7 isotypes, the term "Ara h 7.0101" refers to the isotype having the sequence SEQ ID NO1, and the term "Ara h 7.0" refers to the isotype having the sequence SEQ ID NO3. Any data base codes referred to throughout this application refers to the polypeptide sequence available via the NCBI data bases as online at the priority date of this application. Preferably antibodies are detected in the sample that bind to Ara h 7.0201 according to the present invention, but not to any of the other Ara h 7 isotypes, more specifically Ara h 7.0101 and Ara h 7.0, and the means for specifically capturing an antibody to Ara h 7 isotype 7.0201 is configured for this purpose and is preferably a polypeptide comprising a sequence selected from the group comprising SEQ ID NO8 or a variant thereof, preferably a sequence from the group comprising SEQ ID NO7, SEQ ID NO8, SEQ ID NO6, SEQ ID NO9 and SEQ ID NO10, more preferably SEQ ID NO6, most preferably Ara h 7 isotype 7.0201 or a variant thereof.

Preferably the antibody to Ara h 7 isotype 7.0201 is an antibody to SEQ ID NO6, more preferably a sequence from the group comprising SEQ ID NO7, SEQ ID NO8, SEQ ID NO9 and SEQ ID NO10, most preferably SEQ ID NO8. More preferably, it does not bind to any epitopes shared by the three Ara h 7 isotypes.

In a preferred embodiment, the term "a means for specifically capturing an antibody to [antigen] X and an antibody to [antigen] Y", as used herein, refers to the sum of a means that specifically captures an antibody to [antigen] X, but not one to [antigen] Y, and a means that specifically captures an antibody to [antigen] Y, but not one to [antigen] X.

For example, X could be Ara h 2 and Y could be Ara h 6. In this case, a means for specifically capturing an antibody to Ara h 2 and Ara h 6 would comprise a means for specifically capturing an antibody to Ara h 2 and, in addition, a means for specifically capturing an antibody to Ara h 6. For instance, a line blot coated with Ara h 2 and Ara h 6, spatially separated from each other, is a means for specifically capturing an antibody to Ara h 2 and Ara h 6.

According to the present invention, the carrier comprises one or more means for specifically capturing an antibody, preferably one or more, more preferably two or more, more preferably three or more, more preferably four or more such means, each of them capable of specifically capturing a different antibody. In a most preferred embodiment, the carrier comprises a means for specifically detecting an antibody to Ara h 2, Ara h 7 isotype 7.0201 and Ara h 6. Said means is preferably immobilized on said carrier. In a preferred embodiment, the means for specifically capturing an antibody is a polypeptide comprising or consisting of an antigen to which the antibody to be captured or detected binds or a variant thereof such as from the group comprising Ara h 2, Ara h 7 isotype 7.0201 and Ara h 6, preferably Ara h 7 isotype 7.0201, or a variant thereof. Preferably said polypeptide, when used for the detection of an antibody to Ara h 7 isotype 7.0201, comprises a sequence from the group comprising SEQ ID NO8, more preferably a sequence from the group comprising SEQ ID NO7, SEQ ID NO8, SEQ ID NO9 and SEQ ID NO10, more preferably SEQ ID NO6, most preferably Ara h 7 isotype 7.0201, or a variant thereof. The polypeptide may be a linear peptide or a folded polypeptide, the latter preferably a variant adopting essentially the same fold as Ara h 7 isotype 7.0201 as may be determined by CD spectroscopy. In a preferred embodiment, the peptide or polypeptide comprises an epitope to the antibody to be captured or detected of at least 7, preferably 10, more preferably 15 amino acids. Said antigen, together with the insoluble carrier to which it is attached, may be separated from a reaction mixture, wherein it is contacted with a sample, in a straightforward manner, for example by filtration, centrifugation or decanting. Said antigen may be immobilized in a reversible or irreversible manner. For example, the immobilization is reversible if the molecule interacts with the carrier via ionic interactions which may be masked by addition of a high concentration of salt or if the molecule is bound via a cleavable covalent bond. By contrast, the immobilization is irreversible if the molecule is tethered to the carrier via a covalent bond that cannot be cleaved in aqueous solution. The polypeptide may be indirectly immobilized, for example by immobilizing an antibody or other entity having affinity to the polypeptide, followed by addition of the polypeptide and formation of a polypeptide-antibody complex.

In a preferred embodiment, the carrier is selected from the group comprising a bead, a test strip, a microtiter plate, a microarray, a solid polymer derived from cellulose, a blot, preferably from the group comprising western blot, line blot and dot blot, a glass surface, a slide, a biochip and a membrane, and is most preferably a microtiter plate or a line blot. In another preferred embodiment, the carrier is selected from the group comprising a bead, a test strip, a microtiter plate, a microarray, a solid polymer derived from cellulose, a blot, selected from the group comprising line blot and dot blot, a glass surface, a slide, and a biochip, and is most preferably a microtiter plate or a line blot.

If the diagnostically useful carrier is a bead, a mixture of beads, each carrying one type means for specifically capturing an antibody may be used. The mixture comprises at least one bead carrying a means for specifically capturing an antibody to Ara h 7 isotype 7.0201, preferably to a sequence from the group comprising SEQ ID NO6, more preferably a sequence from the group comprising SEQ ID NO7, SEQ ID NO8, SEQ ID NO9 and SEQ ID NO10, most preferably SEQ ID NO8, or a variant thereof. In addition, the mixture of beads may comprise at least one additional bead, each bead carrying a means for specifically capturing an antibody to one or more from the group comprising Ara h 2, Ara h 6, Ara h 1, Ara h 3, Ara h 9, Ara h 8 and Ara h 5 and a variant thereof, more preferably from the group comprising Ara h 2, Ara h 6, Ara h 1, Ara h 3, Ara h 9 and a variant thereof, most preferably Ara h 2 and/or Ara h 6.

If the diagnostically useful carrier is a bead, the bead may alternatively comprise, in addition to a means for specifically capturing an antibody to Ara h 7 isotype 7.0201, preferably to a sequence from the group comprising SEQ ID NO6, more preferably a sequence from the group comprising SEQ ID NO7, SEQ ID NO8, SEQ ID NO9 and SEQ ID NO10, most preferably SEQ ID NO8, or a variant thereof, at least one more additional means for specifically capturing an antibody, which may be an antibody to one or more from the group comprising Ara h 2, Ara h 6, Ara h 1, Ara h 3, Ara h 9, Ara h 8 and Ara h 5 and a variant thereof, more preferably from the group comprising Ara h 2, Ara h 6, Ara h 1, Ara h 3, Ara h 9 and a variant thereof, most preferably Ara h 2 and/or Ara h 6. Most preferably, such a bead comprises a means for specifically capturing an antibody to Ara h 7 isotype 7.0201, preferably to a sequence from the group comprising SEQ ID NO6, more preferably a sequence from the group comprising SEQ ID NO7, SEQ ID NO8, SEQ ID NO9 and SEQ ID NO10, most preferably SEQ ID NO8, a means for specifically capturing an antibody to Ara h 2 and a means for specifically capturing an antibody to Ara h 6.

However, the teachings of the present invention may not only be carried out using polypeptides, for example Ara h 7 isotype 7.0201, optionally in combination with one or more further antigens such as Ara h 2 and/or Ara h 6, having the exact sequences referred to in this application explicitly, for example by function, name, sequence or accession number, or implicitly, but also using variants of such polypeptides.

In a preferred embodiment, the term "variant", as used herein, may refer to at least one fragment of the full-length sequence referred to, more specifically one or more amino acid or nucleic acid sequence which is, relative to the full-length sequence, truncated at one or both termini by one or more amino acids. Such a fragment comprises or encodes for a peptide having at least 5, 7, 10, 15, 25, 50, 75, 100, 150 or 200 successive amino acids of the original sequence or a variant thereof. The total length of the variant may be at 5, 7, 10, 15, 25, 30, 40, 50, 60, 70, 80, 90, 100 or more amino acids.

In another preferred embodiment, the term "variant" relates not only to at least one fragment, but also a polypeptide or a fragment thereof comprising amino acid sequences, preferably a fragment comprising at least 25, more preferably 50, more preferably 200 successive amino acids, that are at least 40, 50, 60, 70, 75, 80, 85, 90, 92, 94, 95, 96, 97, 98 or 99% identical to the reference amino acid sequence referred to or the fragment thereof, wherein amino acids other than those essential for the biological activity, for example the ability to bind specifically to an antibody of interest, or the fold or structure of the polypeptide are deleted or substituted and/or one or more such essential amino acids are replaced in a conservative manner and/or amino acids are added or deleted such that the biological activity of the polypeptide is at least partially preserved. The state of the art comprises various methods that may be used to align two given nucleic acid or amino acid sequences and to calculate the degree of identity, see for example Arthur Lesk (2008), Introduction to bioinformatics, Oxford University Press, 2008, 3$^{rd}$ edition. In a preferred embodiment, the ClustalW software (Larkin, M. A., Blackshields, G., Brown, N. P., Chenna, R., McGettigan, P. A., McWilliam, H., Valentin, F., Wallace, I. M., Wilm, A., Lopez, R., Thompson, J. D., Gibson, T. J., Higgins, D. G. (2007): Clustal W and Clustal X version 2.0. Bioinformatics, 23, 2947-2948) is used applying default settings.

In a preferred embodiment, variants may, in addition, comprise chemical modifications, for example isotopic labels or covalent modifications such as glycosylation, phosphorylation, acetylation, decarboxylation, citrullination, hydroxylation and the like. The person skilled in the art is familiar with methods for the modification of polypeptides. Moreover, variants may also be generated by way of fusion with other known polypeptides or variants thereof.

The variant of the polypeptide has biological activity. In a preferred embodiment such biological activity is the ability to bind to the respective antibody. For example, a variant of Ara h 7 isotype 7.0201 has the ability to bind specifically to an antibody, preferably IgA, IgE or IgG class antibody, more preferably IgE, IgG1 or IgG4 class antibody, to Ara h 7 isotype 7.0201 in a sample obtained from a subject allergic to peanut, since it comprises epitopes to which said antibody binds. Preferably it comprises an epitope recognized by an antibody in a sample from an allergic patient, which antibody binds to Ara h 7 isotype 7.0201, more preferably to an epitope comprising SEQ ID NO8, most preferably to SEQ ID NO8, and more preferably does not bind not to isotypes 7.0101 or 7.0). The person skilled in the art is capable of designing variants having biological activity by starting from the original Ara h 7 isotype 7.0201 sequence, bearing in mind the importance of SEQ ID NO8, introduce modifications such as point mutations, truncations and the like and subsequently confirm that the variant still has biological activity by testing whether said variant binds to an IgE antibody to Ara h 7 isotype 7.0201 in a sample obtained from a subject allergic to peanut, preferably using an ELISA as described in detail in Example 1.

If a polypeptide is used as the means for specifically capturing an antibody, for example to Ara h 7 isotype 7.0201, said polypeptide, when used to carry out the teachings of the present invention, may be provided in any form and at any degree of purification, from tissues, fruits or cells comprising said polypeptide in an endogenous form, more preferably cells overexpressing the polypeptide, crude or enriched lysates of such cells, to purified and/or isolated polypeptide which may be essentially pure. In a preferred embodiment, the polypeptide is a native polypeptide, wherein the term "native polypeptide", as used herein, refers to a folded polypeptide, more preferably to a folded polypeptide purified from tissues or cells, more preferably from mammalian cells or tissues, optionally from non-recombinant tissues or cell. If a native polypeptide is used, it is preferably enriched compared to its natural state.

According to the present invention, the polypeptide may be a recombinant protein, wherein the term "recombinant", as used herein, refers to a polypeptide produced using genetic engineering approaches at any stage of the production process, for example by fusing a nucleic acid encoding the polypeptide to a strong promoter for overexpression in cells or tissues or by engineering the sequence of the polypeptide itself. The person skilled in the art is familiar with methods for engineering nucleic acids and polypeptides encoded (for example, described in Sambrook, J., Fritsch, E. F. and Maniatis, T. (1989), Molecular Cloning, CSH or in Brown T. A. (1986), Gene Cloning—an introduction, Chapman & Hall) and for producing and purifying native or recombinant polypeptides (for example Handbooks "Strategies for Protein Purification", "Antibody Purification", published by GE Healthcare Life Sciences, and in Burgess, R. R., Deutscher, M. P. (2009): Guide to Protein Purification). In another preferred embodiment, the polypeptide is an isolated polypeptide, wherein the term "isolated" means that the polypeptide has been enriched compared to its state upon production using a biotechnological or synthetic approach and is preferably pure, i.e. at least 60, 70, 80, 90, 95 or 99 percent of the polypeptide in the respective sample consists of said polypeptide as judged by SDS polyacrylamide gel electrophoresis followed by Coomassie blue staining and visual inspection. Preferably any polypeptide on a carrier used as a means to capture an antibody is pure.

In a preferred embodiment, a method, preferably for providing an antibody to Ara h 7 isotype 7.0201, is provided according to the present invention that comprises the steps: a) providing a sample comprising an antibody to Ara h 7 isotype 7.0201, preferably to a sequence from the group comprising SEQ ID NO6, more preferably a sequence from the group comprising SEQ ID NO7, SEQ ID NO8, SEQ ID NO9 and SEQ ID NO10, most preferably SEQ ID NO8, b) contacting the sample with a means for specifically capturing the antibody to Ara h 7 isotype 7.0201, preferably to a sequence from the group comprising SEQ ID NO6, more preferably a sequence from the group comprising SEQ ID NO7, SEQ ID NO8, SEQ ID NO9 and SEQ ID NO10, most preferably SEQ ID NO8, under conditions compatible with formation of a complex comprising the antibody and the means, and c) isolating this complex, optionally followed by release from the complex and/or detection of the antibody.

The subject according to the present invention providing the sample is an organism producing antibodies, preferably IgA, IgE or IgG, more preferably IgE, IgG1 or IgG4 class or equivalent allergy-related antibodies, more preferably a mammal, most preferably a human.

Within the scope of the present invention is a diagnostically useful carrier comprising a means for specifically capturing an antibody to an antigen such as Ara h 7 isotype 7.0201. In a preferred embodiment, the term "specifically capturing an antibody", as used herein, refers to the ability to bind specifically to the antibody of interest to the effect that it is bound and removed from the sample, whereas other antibodies, preferably of the same class, are essentially not bound and remain in the sample.

The diagnostically useful carrier according to the invention serves as a scaffold for the one or more means for specifically capturing an antibody, preferably a diagnostically relevant antibody. Said carrier is suitable for carrying out a diagnostic method. By using a carrier rather than free, soluble means for specifically capturing an antibody, it is more straightforward to isolate and separate from the sample a complex comprising the means and the antibody and to wash said complex, for example for the purpose of removing any molecules binding non-specifically to the means, complex or carrier. In a preferred embodiment, the diagnostically useful carrier is a diagnostic device, preferably selected from the group comprising a bead, a test strip, a microtiter plate, a blot and a membrane, and is preferably a microtiter plate or line blot.

According to the present invention, a means for specifically detecting a captured antibody is provided, optionally as part of a kit. In a preferred embodiment, the term "specifically detecting a captured antibody", as used herein, means that the antibody binding specifically to the means for specifically capturing the antibody, preferably Ara h 7 isotype 7.0201, following capture, is detected rather than any other antibody present in the sample. In a preferred embodiment, the term "binding specifically", as used herein, means that the binding is stronger than a binding reaction characterized by a dissociation constant of $1\times10^{-5}$ M, more preferably $1\times10^{-7}$ M, more preferably $1\times10^{-8}$ M, more preferably $1\times10^{-9}$ M, more preferably $1\times10^{-10}$ M, more preferably $1\times10^{-11}$ M, more preferably $1\times10^{-12}$ M, as determined by surface plasmon resonance using Biacore equipment at 25° C. in PBS buffer at pH 7.

In a preferred embodiment, the means for specifically capturing an antibody to Ara h 7 isotype 7.0201 and the means for specifically capturing an antibody to one or more further antigens are on separate carriers. This means that the means are not attached to a single carrier, but one or more carriers that are separate and/or separable without damaging them. For example, the means for specifically capturing an antibody to Ara h 7 isotype 7.0201 may be attached to a first test strip, and the means for specifically capturing an antibody to Ara h 2 is attached to another test strip which is separate from the first test strip.

In another preferred embodiment, the means for specifically capturing an antibody to Ara h 7 isotype 7.0201 and the means for specifically capturing an antibody to one or more further antigens are on one, preferably covalently linked to one carrier. This means that the means are attached to one carrier which may not be disassembled, without damaging the carrier, such that the means are on separate carriers. For example, the means may be all coated on one test strip, particular in the form of a line blot.

In another preferred embodiment, the diagnostically useful carrier comprises a means for capturing any antibody of the class of antibody to be detected, preferably a means for capturing all IgA, IgG or IgE class, preferably IgE antibodies in the sample.

The assay is carried out such that the sample is contacted with the carrier under conditions allowing binding of all the antibodies in the sample of the class of antibodies comprising the antibody to be detected, more specifically IgA, IgG or IgE class, preferably IgE antibody, followed by washing, followed by specific detection of the antibody to be detected, for example by contacting the carrier with a labeled antigen such as a polypeptide which may be an antibody for specifically detecting an antibody to Ara h 7 isotype 7.0201, preferably SEQ ID NO6, more preferably to a sequence from the group comprising SEQ ID NO7, SEQ ID NO8, SEQ ID NO9 and SEQ ID NO10, most preferably to SEQ ID NO8 or a variant thereof. This antigen then binds to the antibody to be detected which had bound to the carrier. The antibody to be detected may then be detected by detecting the label associated with the antigen. The polypeptide here does not serve to capture the antibody. It was captured beforehand together with all antibodies of the same class. The point of the antigen is merely to make the bound antibody detectable.

The antigen may comprise a detectable label, preferably from the group comprising an enzymatically active, fluorescent, radioactive or chemiluminescent label. Alternatively the antigen may be dissociated from the antibody following specific binding and washing and then its presence or absence may be detected.

The inventive teachings provide a kit, preferably for diagnosing an allergy, more preferably for diagnosing a peanut allergy. Such a kit is a container that comprises specific reagents required to practice the inventive method, in particular the diagnostically useful carrier according to the present invention, optionally in addition to one or more solutions required to practice the inventive method, preferably selected from or all from the group comprising sample dilution buffer, washing buffer and buffer comprising a means for detecting any specifically captured antibody, such as a secondary antibody and optionally a means for detecting the latter. Furthermore, it may comprise instructions detailing how to use the kit and the inventive diagnostically useful carrier for contacting the inventive polypeptide with a bodily fluid sample from a subject, preferably a human subject, for example a line blot, wherein the inventive means for specifically capturing an antibody to Ara h 7 isotype 7.0201, is immobilized on the line blot. Furthermore, the kit may comprise a positive control, for example a recombinant antibody known to bind to Ara h 7 isotype 7.0201, and a negative control, for example a protein having no detectable affinity to Ara h 7 isotype 7.0201 such as bovine serum albumin. Finally, such a kit may comprise a standard solution comprising an Ara h 7 isotype 7.0201-binding antibody for preparing a calibration curve. In a preferred embodiment, the kit comprises a device, preferably a blot-based device such as a line blot coated with a means for specifically capturing an antibody to Ara h 7 isotype 7.0201 and, optionally, an antibody to one or more further antigens such as Ara h 2 and/or Ara h 6.

According to the invention, a means for detecting the one or more captured antibodies is required and may be included in a kit. The person skilled in the art is aware of many methods that may be used, which are also described in the state of the art, for example in Zane, H. D. (2001), Immunology—Theoretical & Practical Concepts in Laboratory Medicine, W. B. Saunders Company, in particular in Chapter 14. In a preferred embodiment, a secondary antibody binding to the constant region of the one or more captured antibodies, which is the corresponding primary antibody, is used, which secondary antibody may be associated with a label that is straightforward to detect, for example a fluorescent, radioactive or enzymatically active label, the latter of which may catalyze a chemiluminescent reaction or the generation of a molecule detectable using colorimetry or spectroscopy or another analytical method. In a more preferred embodiment, the secondary antibody is associated with a label selected from the group comprising a fluorescent, a radioactive and a chemiluminescent label.

Alternatively, a biological functional assay may be used as a means for detecting the one or more captured antibody under the proviso that it is an IgE class antibody, preferably an assay based on basophil activation by IgE antibody. Such assays have been described in the state of the art, for example Hausmann, O. V., Gentinetta. T., Bridts, C. H., and Ebo, E. G. (2009): The Basophil Activation Test in Immediate-Type Drug Allergy, Immunol. Allergy Clin. N. Am. 29, 555-566.

In a preferred embodiment, the term "diagnosis", as used herein, refers to any kind of procedure aiming to obtain information instrumental in the assessment whether a patient suffers or is likely or more likely than the average or a comparative subject, the latter preferably having similar symptoms, to suffer from certain a disease or disorder in the past, at the time of the diagnosis or in the future, to find out how the disease is progressing or is likely to progress in the future or to evaluate the responsiveness of a patient with regard to a certain treatment, for example the administration of suitable drugs such as drugs for the desensitization of allergic patients. In other words, the term "diagnosis" comprises not only diagnosing, but also prognosticating and/or monitoring the course of a disease or disorder. In a more preferred embodiment, the term "diagnosis", as used herein, implies that it is unknown whether the subjected a sample of which is analyzed according to the present invention, has an allergy to nuts, preferably peanut, as evidenced by the presence of antibodies to a peanut-specific allergen in their blood, for example one selected from the group comprising Ara h 2, Ara h 6 and Ara h 7, preferably Ara h 7.

Therefore, the term "diagnosis" does preferably not imply that the diagnostic methods or agents according to the present invention will be definitive and sufficient to finalize the diagnosis on the basis of a single test, let alone parameter, but may refer to a contribution to what is referred to as a "differential diagnosis", i.e. a systematic diagnostic procedure considering the likelihood of a range of possible conditions on the basis of a range of diagnostic parameters. The term "diagnosis" may also refer to a method or agent used to choose the most promising treatment regime for a patient. In other words, the method or agent may relate to selecting a treatment regimen for a subject.

The present invention relates to a method comprising the step detecting in a sample from a subject the presence or absence of an antibody to Ara h 7 isotype 7.0201, preferably to a sequence from the group comprising SEQ ID NO6, more preferably a sequence from the group comprising SEQ ID NO7, SEQ ID NO8, SEQ ID NO9 and SEQ ID NO10, most preferably SEQ ID NO8. Such a method may comprise the steps a) providing a sample from a subject, b) contacting the sample with the diagnostically useful carrier according to the present invention under conditions compatible with the formation of a complex comprising the diagnostically useful carrier and the antibody, more specifically the means for specifically capturing the antibody and the antibody, c) isolating any said complex, for example by removing the sample, d) optionally washing said complex, and e) detecting said complex. The method is preferably an in vitro method. The detection of the complex for the prognosis, diagnosis, methods or test kit according to the present invention comprises the use of a method selected from the group comprising immunodiffusion techniques, basophil activation by IgE antibody, immunoelectrophoretic techniques, light scattering immunoassays, agglutination techniques, labeled immunoassays such as those from the group comprising radiolabeled immunoassay, enzyme immunoassays such as colorimetric assays, chemiluminescence immunoassays and immunofluorescence techniques. In a preferred embodiment, the complex is detected using a method selected from the group comprising immunodiffusion techniques, basophil activation by IgE antibody, immunoelectrophoretic techniques, light scattering immunoassays, agglutination techniques, labeled immunoassays from the group comprising radiolabeled immunoassays, chemiluminescence immunoassays and immunofluorescence techniques. The person skilled in the art is familiar with these methods, which are also described in the state of the art, for example in Zane, H. D. (2001): Immunology—Theoretical & Practical Concepts in Laboratory Medicine, W. B. Saunders Company, in particular in Chapter 14.

In many cases detecting the absence or presence of an antibody, optionally meaning determining whether the concentration of the antibody is beyond a certain threshold preferably as set by measurement using ELISA, preferably as described in Example 1, in the implicit detection limit by this method, often suggested by the detection limit, in the sample, is sufficient for the diagnosis. If the antibody can be detected, this will be information instrumental for the clinician's diagnosis and indicates an increased likelihood that the patient suffers from a disease. In a preferred embodiment, the relative concentration of the antibody in the serum, compared to the level that may be found in the average healthy subject, may be determined. In a preferred embodiment, the term "detecting the presence", as used herein, means that it is sufficient to check whether a signal sufficiently beyond any background level may be detected using a suitable complex detection method that indicates that the antibody of interest is present or more antibody of interest is present than would be in a healthy subject. In a more preferred embodiment this may involve determining whether the concentration is at least 0.1, preferably 0.2, 0.5, 1, 2, 5, 10, 20, 25, 50, 100, 200, 500, 1000, 10000 or 100000 times higher than the concentration of the antibody of interest found in the average healthy subject.

In a preferred embodiment, the absence or presence of at least antibodies, such as an antibody to Ara h 7 isotype 7.0201 and the antibody to Ara h 2 and/or the antibody to Ara h 6, is detected simultaneously, i.e. at the same time. This is convenient in terms of efficient diagnostic procedures, as a maximum of diagnostic information is obtained in a given period of time. Of course, a prerequisite is that sufficient capacity is available for running all reactions.

In a preferred embodiment, the absence or presence of at least two antibodies, such as an antibody to Ara h 7 isotype 7.0201 and the antibody to Ara h 2 and/or the antibody to Ara h 6, is detected in spatially separate reactions. This means that these reactions run in different reaction mixtures in separate vessels.

If more than one antibody is to be detected, the method may be carried out in a one-pot reaction. Preferably, the term "one-pot reaction", as used herein, means that two or more, preferably all reactions carried out for the purpose of detecting the presence or absence of an antibody are carried out in the same reaction mixture in one reaction vessel, without physical barriers between the reactions, by contrast to experimental settings contemplating that at least two reactions are carried out in separate solutions and reaction vessels.

The antibody to be detected may be a monospecific antibody. In a preferred embodiment, the term "monospecific antibody", as used herein, refers to an antibody binding to one antigen only, preferably one diagnostically relevant antigen only, more preferably only one diagnostically relevant antigen from the group comprising Ara h 7, Ara h 2 and Ara h 6. In a more preferred embodiment, the monospecific antibody to be detected may bind to Ara h 7 isotype 7.0201, preferably to SEQ ID NO6, more preferably to a sequence from the group comprising SEQ ID NO7, SEQ ID NO8, SEQ ID NO9 and SEQ ID NO10, most preferably to SEQ ID NO8, but not any other allergen such as isotypes Ara h 70101, Ara h 7.0, or such as Ara h 2 and/or Ara h 6. If a patient has a monospecific antibody only, their allergy can only be detected, by way of serology, if a means for specifically capturing and detecting said monospecific antibody is used. If a diagnostic assay based on means to detect antibodies to Ara h 7 isotypes other than 7.0201, which do not comprise SEQ ID NO8, are used, the result of the assay may be false-negative, since the antibody monospecific to Ara h 7 isotype 7.0201, more preferably SEQ ID NO8, cannot be detected.

The invention provides a use of a means for specifically capturing an antibody to Ara h 7 isotype 7.0201, which is preferably a polypeptide comprising Ara h 7 isotype 7.0201 or variant thereof, for increasing the sensitivity of a diagnostically useful carrier, for detecting an antibody to Ara h 7, preferably a monospecific antibody to Ara h 7, for manufacturing a kit for the diagnosis of peanut allergy or for a method for diagnosing a nut allergy, preferably a peanut allergy, optionally in combination with a means for specifically capturing an antibody to one or more further antigens such as Ara h 2 and/or Ara h 6.

The invention provides a use of an antibody binding specifically to Ara h 7 isotype 7.0201, preferably SEQ ID NO6, more preferably to a sequence from the group comprising SEQ ID NO7, SEQ ID NO8, SEQ ID NO9 and SEQ ID NO10, most preferably to SEQ ID NO8, which antibody is preferably a monospecific antibody. More preferably the antibody is detected in or isolated from a patient sample and is an IgA, IgE or IgG class antibody, more preferably an IgE, IgG1 or IgG4 class antibody, most preferably an IgE class antibody.

The invention provides an antibody or fragment thereof binding specifically to Ara h 7 isotype 7.0201, preferably SEQ ID NO6, more preferably to a sequence from the group comprising SEQ ID NO7, SEQ ID NO8, SEQ ID NO9 and SEQ ID NO10, most preferably to SEQ ID NO8, which antibody is preferably a monospecific antibody. The antibody may be a monoclonal antibody. The antibody may be a polyclonal antibody. This antibody is useful for many diagnostic applications, for example for measuring avidity of an antibody from a sample. Alternatively, the antibody may be used for a competitive assay such as a competitive ELISA. Alternatively, the antibody may be used to immobilize a polypeptide comprising preferably SEQ ID NO6, more preferably to a sequence from the group comprising SEQ ID NO7, SEQ ID NO8, SEQ ID NO9 and SEQ ID NO10, most preferably to SEQ ID NO8. Alternatively, the antibody may be used as a positive control. The person skilled in the art is aware how to obtain such an antibody, for example using recombinant methods. The manufacture may involve the step purifying and/or isolating the antibody.

The invention provides a pharmaceutical composition, preferably a vaccine, comprising Ara h 7 isotype 7.0201, preferably a polypeptide comprising SEQ ID NO6, more preferably a sequence from the group comprising SEQ ID NO7, SEQ ID NO8, SEQ ID NO9 and SEQ ID NO10, most preferably SEQ ID NO8, or a variant thereof, optionally in combination with one or more further antigens such as Ara h 2 and/or Ara h 6 or a variant thereof, which composition is preferably suitable for administration to a subject, preferably a mammalian subject, more preferably to a human. Such a pharmaceutical composition may comprise a pharmaceutically acceptable carrier. The pharmaceutical composition may, for example, be administered orally, parenterally, by inhalation spray, topically, by eyedrops, rectally, nasally, buccally, vaginally or via an implanted reservoir, wherein the term "parentally", as used herein, comprises subcutaneous, intracutaneous, intravenous, intramuscular, intra-articular, intrasynovial, instrasternal, intrathecal, intralesional and intracranial injection or infusion techniques. The pharmaceutical composition may be provided in suitable dosage forms, for example capsules, tablets and aqueous suspensions and solutions, preferably in sterile form. It may be used in a method of treatment of a disease, preferably an allergy, which method comprises administering an effective amount of the inventive polypeptide to a subject. A hypoallergenic variant of Ara h 7 and, optionally, one or more further antigens such as Ara h 2 and/or Ara h 6 may be used. The person skilled in the art is familiar with methods for the generation of hypoallergenic variants of known allergens.

The invention provides a vaccine comprising Ara h 7 isotype 7.0201, more preferably a polypeptide comprising SEQ ID NO6, more preferably a sequence from the group comprising SEQ ID NO7, SEQ ID NO8, SEQ ID NO9 and SEQ ID NO10, most preferably SEQ ID NO8.

For therapeutic purposes, a vaccine may be provided that comprises the polypeptide comprising to Ara h 7 isotype 7.0201, preferably SEQ ID NO6, more preferably to a sequence from the group comprising SEQ ID NO7, SEQ ID NO8, SEQ ID NO9 and SEQ ID NO10, most preferably to SEQ ID NO8 or a variant thereof may be formulated with one or more diluents, one or more glidants, and/or one or more filling agents. The preparation of suitable formulations is described in U.S. Pat. No. 9,198,869, incorporated herein by reference in its entirety. A hypoallergenic variant may be prepared as described in the state of the art, for example in EP 1440979, which is also incorporated by reference in its entirety.

A vaccine may be produced using a method of making a low dose capsule formulation useful in the methods provided here, comprising, (a) mixing peanut flour and Ara h 7 isotype 7.0201, preferably SEQ ID NO6, more preferably to a sequence from the group comprising SEQ ID NO7, SEQ ID NO8, SEQ ID NO9 and SEQ ID NO10, most preferably to SEQ ID NO8 or a variant thereof and diluent in a first blend; (b) adding about 45% of diluent in a second blend; (c) adding remaining diluent in a third blend; (d) adding a glidant and/or lubricant in a final blend; and (e) encapsulating blended powder in a capsule. In one embodiment, the diluent of step (a) comprises starch or lactose, microcrystalline cellulose (Avicel®), or dicalcium phosphate. In another embodiment, the diluent of step (b) and/or (c) comprises starch, lactose, microcrystalline cellulose (Avicel®), or dicalcium phosphate. In another embodiment, the glidant of step (d) glidant of step (d) comprises colloidal silicon dioxide (Cab-O-Sil), talc (e.g., Ultra Talc 4000), or combinations thereof. In another embodiment, the lubricant of step (d) comprises magnesium stearate. In one non-limiting example, the glidant comprises Cab-O-Sil. In one embodiment, step (d) comprises adding a glidant or a lubricant. In another embodiment, step (d) comprises adding a glidant and a lubricant. In another embodiment, the method further comprises sampling the blended mixture one or more times prior to encapsulation. In another embodiment, the dose comprises about 0.5 or about 1.0 mg peanut protein. In another embodiment of the described methods, step (d) further comprises passing the blended material through a mesh screen (see U.S. Pat. No. 9,198,869, incorporated herein by reference in its entirety).

In another embodiment, the diluent include, but are not limited to, alginic acid and salts thereof; cellulose derivatives such as carboxymethylcellulose, methylcellulose (e.g., Methocel®), hydroxypropylmethylcellulose, hydroxyethylcellulose, hydroxypropylcellulose (e.g., Klucel®), ethylcellulose (e.g., Ethocel®), microcrystalline cellulose (e.g., Avicel®); silicified microcrystalline cellulse; microcrystalline dextrose; amylose; magnesium aluminum silicate; polysaccharide acids; bentonites; gelatin; polyvinylpyrrolidone/vinyl acetate copolymer; crosspovidone; povidone; starch; pregelatinized starch; tragacanth, dextrin, a sugar, such as sucrose (e.g., Dipac®), glucose, dextrose, molasses, mannitol, sorbitol, xylitol (e.g., Xylitab®), lactose (e.g., lactose monohydrate, lactose anhydrous, etc.); dicalcium phosphate; a natural or synthetic gum such as acacia, tragacanth, ghatti gum, mucilage of isapol husks, polyvinylpyrrolidone (e.g., Polyvidone® CL, Kollidon® CL, Polyplasdone® XL-10), larch arabogalactan, Veegum®, polyethylene glycol, waxes, sodium alginate, a starch, e.g., a natural starch such as corn starch or potato starch, a pregelatinized starch such as Colorcon (Starch 1500), National 1551 or Amijel®, or sodium starch glycolate such as Promogel® or Explotab®; a cross-linked starch such as sodium starch glycolate; a cross-linked polymer such as crospovidone; a cross-linked polyvinylpyrrolidone; alginate such as alginic acid or a salt of alginic acid such as sodium alginate; a clay such as Veegum® HV (magnesium aluminum silicate); a gum such as agar, guar, locust bean, Karaya, pectin, or tragacanth; sodium starch glycolate; bentonite; a natural sponge; a surfactant; a resin such as a cation-exchange resin; citrus pulp; sodium lauryl sulfate; sodium lauryl sulfate in combination starch; and combinations thereof. In one embodiment, the formulation comprises microcrystalline cellulose or starch 1500. In another embodiment, the formulation comprises microcrystalline cellulose and starch 1500.

Alternatively, a method of preparing a liquid formulation for preventing or treating allergy in a subject by oromucosal administration may be used to make vaccine, the formulation comprising Ara h 7 isotype 7.0201, preferably SEQ ID NO6, more preferably to a sequence from the group comprising SEQ ID NO7, SEQ ID NO8, SEQ ID NO9 and SEQ ID NO10, most preferably to SEQ ID NO8 or a variant thereof and an adjuvant selected from the group consisting of oxygen-containing metal salts, the method comprising dissolving the oxygen-containing metal salt in a solvent, adding the allergen and allowing the allergen and oxygen-containing metal salt to react for a period of time. The oxygen-containing metal salt can be designed to have specific preference for specific mucosal tissues e.g. GALT and Peyers patch, further enhancing the delivery of the active substances at a relevant target site (mucosal tissue). For several of the oxygen-containing metal salts (e.g. $Al(OH)_3$, $AlPO_4$, $Ca_3PO_4$) the particle size range is between 0.5 and 15 μm. The oxygen-containing metal salt imparts a gel-like structure on the liquid vaccine formulation thereby making it easier to keep in place in the mouth, in particular under the tongue, for the required period of time, and hence it facilitates treatment protocol compliance and correct dosing (see US2006/0115499A1, incorporated herein by reference in its entirety).

Another embodiment of the invention relates to a hypoallergenic. For example, a hypoallergenic may be prepared in the form of a mosaic antigen in a process, whereby a) in a first step the allergen is split into at least two parts and the IgE reactivity of each part is determined and b) in a second step those parts of the allergen which have no detectable IgE reaction are combined to a mosaic antigen which comprises the amino acids of the allergen but the order of the amino acids of the mosaic antigen is different from that of the naturally occurring allergen.

A mosaic antigen as prepared by the described process can be formulated as a medicament for the treatment of an allergic reaction. The main component is the mosaic antigen which is preferably administered together with an adjuvant. There are several adjuvants which are suitable for the application to humans like e.g. aluminum hydroxide gel. In another embodiment of the present invention it is also possible to link the mosaic antigen directly by covalent binding to another component which generally enhances the immunologic reaction of the body (see EP1440979B1, incorporated herein by reference in its entirety).

Alternatively, hypoallergenic recombinant allergens may be made in a method, whereby the antigen converted into a conformation in the course of this process, which has no or greatly reduced affinity for IgE for the same T-cell stimulation. This may be achieved by means of one or more chromatographic purification steps using essentially unbuffered aqueous bases as eluent and subsequent neutralization, whereby crude recombinant antigen extract is used (see EP1478662A1, incorporated herein by reference in its entirety).

The invention provides a method for treating, preventing or ameliorating an allergy, preferably a nut allergy, more preferably a peanut allergy, but administering to a subject the inventive pharmaceutical composition.

The invention provides a use of Ara h 7 isotype 7.0201, more preferably a polypeptide comprising SEQ ID NO8, more preferably a sequence from the group comprising SEQ ID NO7, SEQ ID NO6, SEQ ID NO9 and SEQ ID NO10, more preferably SEQ ID NO6, most preferably Ara h 7 isotype 7.0201 or variant thereof, preferably in combination with Ara h 2 and/or Ara h 6 or a variant thereof, for the manufacture of a kit for the diagnosis of peanut allergy, in which a diagnostic assay with an increased sensitivity is provided. Such manufacture may relate to a method comprising the step immobilizing on a diagnostically useful carrier Ara h 7 isotype 7.0201, more preferably a polypeptide comprising SEQ ID NO6, more preferably a sequence from the group comprising SEQ ID NO7, SEQ ID NO8, SEQ ID NO9 and SEQ ID NO10, most preferably SEQ ID NO8, preferably in combination with Ara h 2 and/or Ara h 6 or a variant thereof.

The invention provides a use of Ara h 7 isotype 7.0201, more preferably a polypeptide comprising SEQ ID NO8, more preferably a sequence from the group comprising SEQ ID NO7, SEQ ID NO6, SEQ ID NO9 and SEQ ID NO10, more preferably SEQ ID NO6, most preferably Ara h 7 isotype 7.0201, or a variant thereof, preferably in combination with Ara h 2 and/or Ara h 6 or a variant thereof, for the manufacture of a medicament, preferably a vaccine, which is preferably for preventing, ameliorating or treating allergic conditions, in particular a nut allergy, more specifically a peanut allergy.

Figure 3:
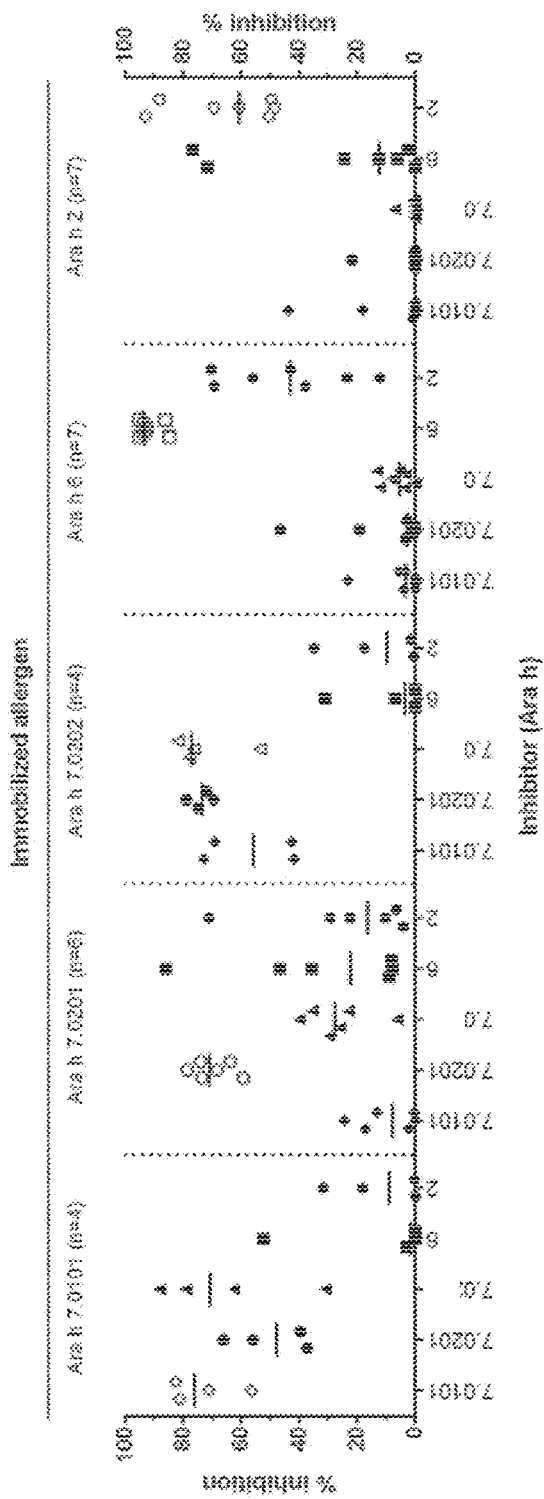

FIG. 3 shows inhibition experiments described in example 3. Maximum inhibition observed for the five peanut components in patients sensitized to the allergen that was immobilized. Horizontal line marks the median value. The grey, open markers indicate inhibition with the same allergen as the one immobilized.

FIG. 4 shows the results of epitope mapping of serum IgE against linear peptides of Ara h 7.0201 C-terminus. The normalized signal-to-noise ratio (z-score) is presented for every peptide on the microarray. Positive binding requires at least 6 subsequent peptides yielding a z-score above 3.

SEQUENCES

The present invention comprises a range of novel polypeptides, more specifically SEQ ID NO 1 (expressed sequence without signal sequence of Ara h 7.0101)
TRWDPDRGSRGSRWDAPSRGDDQCQRQLQRANLRPCEEHNIRRRVEQEQ
EQEQDEYPYSRRGSRGRQPGESDENQEQRCCNELNRFQNNQRCMCQALQ
QILQNQSFWVPAGQEPVASDGEGAQELAPELRVQVTKPLRPL SEQ ID NO 2 (expressed sequence without signal sequence of Ara h 7.0201)
TRWDPDRGSRGSRWDAPSRGDDQCQRQLQRANLRPCEEHIRQRVEKEQ
EQEQDEYPYIQRGSRGRPGESDEDQEQRCCNELNRFQNNQRCMCQALQ
QILQNQSFRFQQDRSQLHQMERELRNLPQNCGFRSPSRCDLSSRTPY SEQ ID NO 3 (expressed sequence without signal sequence of Ara h 7.0)
TRWDPDRGSRGLRWDAPSRGDDQCQRQLQRANLRPCEEHIRQRVEQEQE
QEQDEYPYSQRGSRGRRPGESDEDQEQRCCNELNRFQNNQRCMCQALQQ
ILQNQSFRFQQDRSQLHQNGEGAQELAPELRVQVTKPLRP SEQ ID NO 4 (expressed sequence without signal sequence of Ara h 2.0201)
RQQWELQGDRRCQSQLERANLRPCEQHLMQKIQRDEDSYGRDPYSPSQD

PYSPSQDPDRRDPYSPSPYDRRGAGSSQHQERCCNELNEFENNQRCMCE

ALQQIMENQSDRLQGRQQEQQFKRELRNLPQQCGLRAPQRCDLEVESGG

RDRY

SEQ ID NO 5 (expressed sequence without signal sequence of Ara h 6.0101)
MRRERGRQGDSSSCERQVDRVNLKPCEQHIMQRIMGEQEQYDSYDIRST
RSSDQQQRCCDELNEMENTQRCMCEALQQIMENQCDRLQDRQMVQQFKR
ELMNLPQQCNFRAPQRCDLDVSGGRC SEQ ID NO 6 (C-terminus of Ara h 7 isotype 7.0201)
HQMERELRNLPQNCGFRSPSRCDLSSRTPY SEQ ID NO 7 (Ctermnus of Ara h 7 isotype 7.0201)
NCGFRSPSRC SEQ ID NO 8 (reactive epitope from C-terminus of Ara h 7 isotype 7.0201)
GFRSPS SEQ ID NO 9 (C-terminus of Ara h 7 isotype 7.0201)
CGFRSPSRCD SEQ ID NO10 (C-terminus of Ara h 7 isotype 7.0201)
QNCGFRSPSRCDL SEQ ID NO 11 (Ara h 7 isotype 7.0101, as expressed in example 1)
MSHHHHHHHHLEVLFQGPSMTRWDPDRGSRGSRWDAPSRGDDQCQRQLQR

ANLRPCEEHMRRRVEQEQEQEQDEYPYSRRGSRGRQPGESDENQEQRCCN

ELNRFQNNQRCMCQALQQILQNQSFWVPAGQEPVASDGEGAQELAPELRV

QVTKPLRPL

SEQ ID NO 12 (Ara h 7 isotype 7.0201, as expressed in example 1)
MSHHHHHHHHLEVLFQGPSMTRWDPDRGSRGSRWDAPSRGDDQCQRQLQR

ANLRPCEEHIRQRVEKEQEQEQDEYPYIQRGSRGQRPGESDEDQEQRCCN

ELNRFQNNQRCMCQALQQILQNQSFRFQQDRSQLHQMERELRNLPQNCGF

RSPSRCDLSSRTPY

SEQ ID NO 13 (Ara h 7 isotype 7.0, as expressed in example 1)
MSHHHHHHHHLEVLFQGPSMTRWDPDRGSRGLRWDAPSRGDDQCQRQLQR
ANLRPCEEHIRQRVEQEQEQEQDEYPYSQRGSRGRRPGESDEDQEQRCCN
ELNREQNNQRCMCQALQQILQNQSFREQQDRSQLHQNGEGAQELAPELRV
QVTKPLRP SEQ ID NO 14 (Ara h 2 isotype 2.0201, as expressed in example 1)
MSHHHHHHIEGRTMRQQWELQGDRRCQSQLERANLRPCEQHLMQKIQRDE

DSYGRDPYSPSQDPYSPSQDPDRRDPYSPSPYDRRGAGSSQHQERCCNEL

NEFENNQRCMCEALQQIMENQSDRLQGRQQEQQFKRELRNLPQQCGLRAP

QRCDLEVESGGRDRY

SEQ ID NO 15 (Ara h 6 isotype 6.0101, as expressed in example 1)
MSHHHHHHHFILEVLFQGPSMRRERGRQGDSSSCERQVDRVNLKPCEQHI
MQRIMGEQEQYDSYDIRSTRSSDQQQRCCDELNEMENTQRCMCEALQQIM
ENQCDRLQDRQMVQQFKRELMNLPQQCNFRAPQRCDLDVSGGRC SEQ ID NO 16: Ara h 1.01.01 as used in example 3
MSHHHHHHIEGRTMKSSPYQKKTENPCAQRCLQSCQQEPDDLKQKACESR

CTKLEYDPRCVYDPRGHTGTTNQRSPPGERTRGRQPGDYDDDRRQPRREE

GGRWGPAGPREREREEDWRQPREDWRRPSHQQPRKIRPEGREGEQEWGTP

GSHVREETSRNNPFYFPSRRESTRYGNQNGRIRVLQRFDQRSRQFQNLQN

-continued

HRIVQIEAKPNTLVLPKHADADNILVIQQGQATVTVANGNNRKSENLDEG

HALRIPSGFISYILNRHDNQNLRVAKISMPVNTPGQFEDFFPASSRDQSS

YLQGFSRNTLEAAFNAEFNEIRRVLLEENAGGEQEERGQRRWSTRSSENN

EGVIVKVSKEHVEELTKHAKSVSKKGSEEEGDITNPINLREGEPDLSNNE

GKLFEVKPDKKNPQLQDLDMMLTCVEIKEGALMLPHENSKAMVIVVVNKG

TGNLELVAVRKEQQQRGRREEEEDEDEEEEGSNREVRRYTARLKEGDVFI

MPAAHPVAINASSELHLIGFGINAENNHRIFLAGDKDNVIDQIEKQAKDL

AFPGSGEQVEKLIKNQKESHEVSARPQSQSQSPSSPEKESPEKEDQEEEN

QGGKGPLLSILKAFN

SEQ ID NO 17: Ara h 3.01.01 as used in example 3
MSHHHHHHHHLEVLFQGPSMRQQPEENACQFQRLNAQRPDNRIESEGGYI

ETWNPNNQEFECAGVALSRLVLRRNALRRPFYSNAPQEIFIQQGRGYFGL

IFPGCPRHYEEPHTQGRRSQSQRPPRRLQGEDQSQQQRDSHQKVHREDEG

DLIAVPTGVARNLYNDHDTDVVAVSLTDTNNNDNQLDQFPRRENLAGNTE

QEFLRYQQQSRQSRRRSLPYSPYSPQSQPRQEEREFSPRGQHSRRERAGQ

EEENEGGNIFSGFTPEFLEQAFQVDDRQIVQNLRGETESEEEGAIVTVRG

GLRILSPDRKRRADEEEEYDEDEYEYDEEDRRRGRGSRGRGNGIEETICT

ASAKKNIGRNRSPDIYNPQAGSLKTANDLNLLILRWLGPSAEYGNLYRNA

LEVAHYNTNAHSIIYRLRGRAHVQVVDSNGNRVYDEELQEGHVLWPQNFA

VAGKSQSENFEYVAFKIDSRPSIANLAGENSVIDNLPEEVVANSYGLQRE

QARQLKNNNPFKFFVPPSQQSPRAVA

The present invention is further illustrated by the following non-limiting examples from which further features, embodiments, aspects and advantages of the present invention may be taken.

1. Example 1: Detection of IgE Antibodies to Ara h 7 Isotypes in Sera from Peanut-Sensitized Patients by ELISA

1.1. Recombinant Proteins

Heterologous Expression and Purification of Recombinant Allergens

Ara h 7.0101 (SEQ ID NO11), Ara h 7.0201 (SEQ ID NO12), Ara h 7.0 (SEQ ID NO13), Ara h 6 (SEQ ID NO15) and Ara h 2 (SEQ ID NO14) were expressed and purified as His6 fusion proteins having the sequences indicated by the respective SEQ ID NOs in *E. coli* as described by Sitaru C, Dähnrich C, Probst C, Komorowski L, Blöcker I, Schmidt E, Schlumberger W, Rose C, Stöcker W, Zillikens D. Enzyme-linked immunosorbent assay using multimers of the 16th non-collagenous domain of the BP180 antigen for sensitive and specific detection of pemphigoid autoantibodies. Exp Dermatol. 2007 September; 16(9):770-7. Purification was carried out under denaturing conditions by means of immobilized metal ion chromatography.

1.2. Detection IgE Binding by Means of ELISA

Figure 1:
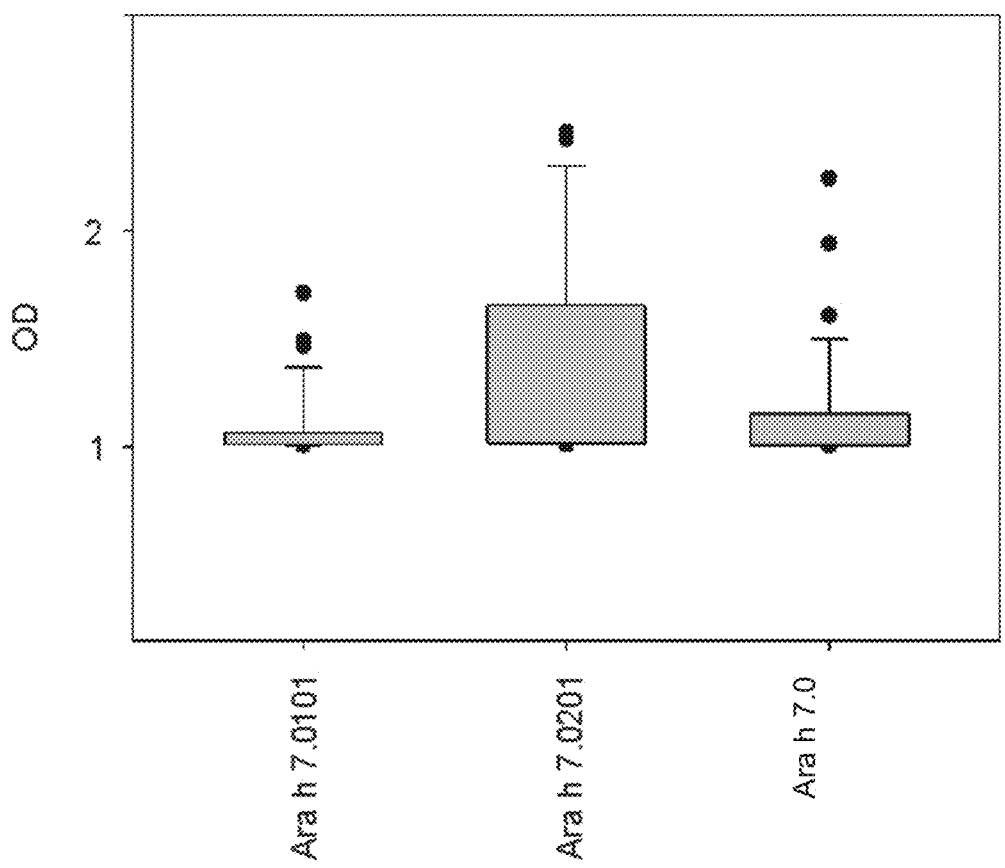
FIG. 1 shows IgE binding to the Ara h 7 isoforms of peanut sensitized patients detected by means of ELISA as described in example 1.

The IgE binding ability of the three Ara h 7 isoforms was analysed by enzyme-linked immunosorbend assay (ELISA) incubated with sera of 33 patients who were IgE positive for peanut extract (FIG. 1). In addition, 10 sera of atopic patient without peanut sensitization and 23 healthy blood donors were incubated as negative controls (all reacted negative, data not shown).

Microtiter plates were coated with the recombinant peanut allergens (9 µg/ml in PBS, pH 7.5) 2 h at 4° C. as described by Sitaru et al. Sera were diluted v/v 1/10 in blocking-buffer (PBS-0.1% bovine serum albumin), 100 µl per well applied in duplicates to the plates and allowed to react over night at 4° C.

Bound antibodies were detected using anti-human IgE peroxidase conjugate and stained with tetramethylbenzidine (Total IgE ELISA EV 3840-9601 E, Euroimmun, Lubeck, Germany). The optical density (OD) was read at 450 nm with reference at 620 nm using an automated spectrophotometer (Spectra Mini, Tecan, Germany).

Results

IgE reactivity against Ara h 7 isotype 7.0101, Ara h 7 isotype 7.0201 and Ara h 7.0 were measured in 66 human Sera. None of the 23 blood donors and none of the 10 sera from allergic patient who had no IgE against peanut extract reacted positive. Of the 23 peanut extract positive sera 11 showed positive results with Ara h 7.0201, but only 6 and 10 with Ara h 7.0101 and Ara h 7, respectively.

Among the positive reacting sera the average OD was 1.0 for Ara h 7.0201. The average OD for Ara h7.0101 and Ara h 7.0 was quite lower (both 0.4).

These results show, on the one hand, that Ara h 7.0201 reacted stronger with the patient IgE and, on the other hand, that more patients could be correctly diagnosed by detection of IgE antibodies using Ara h7.0201 as target antigen compared to the other two isoforms (FIG. 1). In fact, some patients can only (!) be identified and diagnosed as allergic if antibodies to Ara h 7.0201 are detected.

Example 2: Detection of IgE Antibodies by Line Blot

The IgE binding ability of the 2S albumins Ara h 2, Ara h 6, and three Ara h 7 isoforms were investigated by immunoblot analysis. Serum samples from 34 peanut sensitized subjects (FIG. 2) were incubated with Line blot-immunoblots and intensities were evaluated with the EUROLINEScan software. In addition, 20 sera of atopic subjects without peanut sensitization and 17 healthy blood donors were incubated as negative controls (all negative, data not shown).

For the Line blot immunoblots, the recombinant allergens were coated on nylon-based membranes using standard methods. Afterwards the membranes were blocked, dried and fixed on a foil. This foil was cut into strips which were incubated with serum.

Manual incubation of serum samples was carried out according to the EUROIMMUN immunoblot instructions (for Example in DPA-Dx pollen 1, DP 3210-1601-1 E). All incubation and washing steps were done on a rocking shaker at room temperature (+18° C. to +25° C.). Reagents were taken from a kit supplied by EUROIMMUN (DPA-Dx pollen 1, DP 3210-1601-1 E). The immunoblot strips were preincubated with working strength universal buffer (WSUB) for 5 minutes. After removing all liquid strips were in a first step incubated with 100 µl of each serum sample diluted with 1.0 ml WSUB overnight (12 to 24 h). In a second step the strips were incubated with 1.0 ml enzyme conjugate (alkaline phosphatase-conjugated antihuman IgE) for 60 minutes. After step one and two the liquid was respectively aspirated off and the strips were washed for 3×5 minutes with 1.0 ml WSUB. In the third step the strips were incubated with 1.0 ml chromogen/substrate solution for 10 minutes. Afterwards the liquid was again aspirated off and the enzyme reaction was stopped by washing each strip 3×1 minute with deionised or distilled water. Finally the test strips were placed on the evaluation protocol, air dryed and evaluated with the EUROLINESScan software.

Results

In total 71 samples were analysed with the immunoblot. In none of the 20 sera from atopic subjects without specific IgE (sIgE) against peanut extract and the 17 healthy blood donors sIgE against Ara h 2, Ara h 6, and all three isoforms of Ara h 7 was detected. Of the 34 samples from subjects with sIgE against peanut extract 17 samples reacted positive with Ara h 2 and Ara h 6, 15 with Ara h 7.0201, 14 with Ara h 7.0101 and 11 with Ara h 7.0, respectively.

Figure 2:
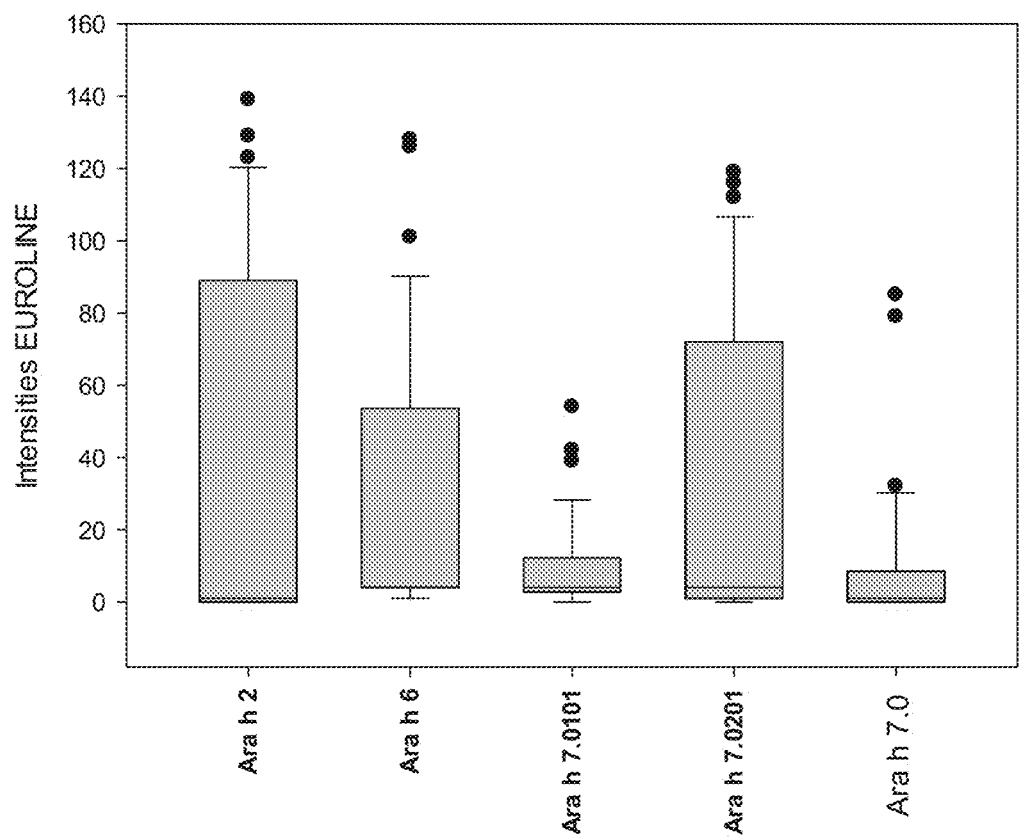
FIG. 2 shows IgE binding to the Ara h 7 isoforms as well as Ara h 2 and Ara h 6 of peanut-sensitized patients detected by means of line blot as described in example 2.

While among the positive reacting sera the mean of immunoblot intensities from Ara h 2, Ara h 6 and Ara h 7.0201 was 84, 59, and 74, average intensities from Ara h 7.0101 and Ara h 7 were quite lower (20 and 28) (FIG. 2).

The results show that subjects with sIgE against peanut extract present higher average IgE levels of Ara h 7.0201 than of Ara h 7.0101 and Ara h 7.0. Furthermore, peanut extract IgE positive subjects have very similar average levels of Ara h 2 and Ara h 7.0201 IgE indicating that Ara h 7.0201 IgE is another major allergen component for peanut allergy as well as Ara h 2.

Example 3: Study Based on Larger Patient Cohort Using Lineblot and EUSA

Patient Selection

To evaluate the diagnostic value of the different peanut storage proteins, adults with a suspected peanut allergy based on history and/or sensitization who had undergone a diagnostic open or double-blind placebo-controlled food challenge (DBPCFC) with peanut in the University Medical Center Utrecht between 2003 and September 2014 were selected (n=127). Residual serum after routine blood collection one year before or after the food challenge date was available for 95 subjects. From this cohort, 40 peanut allergic and 40 tolerant patients (i.e. with a positive and negative challenge respectively) were selected based on availability of ImmunoCAP ISAC sensitization data. The DBPCFCs were performed in accordance with the international consensus protocol as described before (Taylor S L, Hefle S L, Bindslev-Jensen C, Atkins F M, Andre C, Bruijnzeel-Koomen C, et al. A consensus protocol for the determination of the threshold doses for allergenic foods: How much is too much? Clin Exp Allergy 2004; 34:689-95. doi:10.1111/j.1365-2222.2004.1886.x.). All positive challenges were DBPCFCs. Negative challenges also included two open peanut challenges. For the inhibition experiments, serum was gathered from 10 allergic adults sensitized to peanut extract and with a positive DBPCFC, randomly selected from a cohort previously characterized by Peeters K A B M, Koppelman S J, van Hoffen E, van der Tas C W H, den Hartog Jager C F, Penninks A H, et al. Does skin prick test reactivity to purified allergens correlate with clinical severity of peanut allergy? Clin Exp Allergy 2007; 37:108-15. doi:10.1111/j.1365-2222.2006.02628.x.

Line Blot

Sensitization to recombinant peanut storage proteins Ara h 1.0101, 2.0201, 3.0101, 6.0101 and Ara h 7 isotype 7.0201 (Table 1) was assessed using a line blot as described in example 2. Briefly, the test strips were incubated at room temperature on an orbital shaker overnight with 100 μl of patient sera diluted 1:11 in dilution buffer. After washings, an incubation with an enzyme-labelled anti-human IgE antibody, and then with the substrate nitro-blue tetrazolium/ 5-bromo-4-chloro-3'-indolyphosphate, the reaction was evaluated using the software "EUROLineScan". The intensity of the bands was reported as an intensity level and a class, corresponding to the Enzyme-Allergo-Sorbent Test classification (class 0-6) (Williams P B, Barnes J H, Szeinbach S L, Sullivan T J. Analytic precision and accuracy of commercial immunoassays for specific IgE: Establishing a standard. J Allergy Clin Immunol 2000; 105:1221-30. doi: 10.1067/mai.2000.105219). A class of 1 or higher, corresponding to intensity level of 3 or higher, was considered positive.

Heterologous Expression and Purification of Recombinant Allergens

Ara h 7.0101 (SEQ ID NO11), Ara h 7.0201 (SEQ ID NO12), Ara h 7 (SEQ ID NO13), Ara h 6 (SEQ ID NO15) and Ara h 2 (SEQ ID NO14) were expressed without signal sequence as fusion proteins with N-terminal His(6×) in $E.$ $coli$ with represented by the respective SEQ ID NOs as described by Sitaru et al. (2007). Purification was carried out under denaturing conditions by means of immobilized metal ion chromatography. For inhibition experiments recombinant proteins were dialyzed against TBS (20 mM Tris-HCl, pH 7.4, 150 mM NaCl, 3% Sucrose, 1.2 mM Glutathion, non-reduced, 3.8 mM Glutathion, reduced).

ELISA and Inhibition Experiment

Microtiter plates were coated with immobilized recombinant peanut allergens (9 μg/ml in PBS, pH 7.5) 2 h at 4° C. as described by Sitaru et al .

For dose-dependent cross-inhibition experiments, optimal diluted sera in blocking buffer described in example 1 (see Table 3) were pre-incubated with the competing allergens at final concentration of 0.1, 1 and 10 μg/ml, for 30 min under shaking at room temperature before applying to the plates. Inhibition values are given as a percentage reduction of OD compared to the controls, in which only blocking buffer has been added.

Data Analysis and Statistics

Spearman correlation was used to analyze the correlation between results of the sIgE tests. The chi-squared test was used to assess differences in positive tests between tolerant and allergic patients. The area under the receiver operating characteristic (ROC) curve (AUC) was determined to evaluate the ability of the tests to discriminate between allergic and tolerant, as established by food challenge. SPSS Statistics 21 (IBM Corporation, Armonk, N.Y., USA) was used to perform the analyses.

Results

Evaluation of Sensitization to Peanut Storage Proteins

Patient characteristics of the 80 peanut challenged patients, used in the diagnostic evaluation, are listed in Table 2. Median age was 25 years (range: 16-77) and 36% was male. Sensitization to all peanut storage proteins occurred significantly more often in the peanut allergic group. In the peanut allergic group, 73% was sensitized to at least one of the five storage proteins, compared to 15% in the peanut tolerant group. Peanut 2S albumin Ara h 2 was most recognized in the peanut allergic patients (65%), closely followed by the other two 2S albumins Ara h 6 and 7 (both 60%).

The highest discriminative value was found for Ara h 6 (AUC 0.85), followed by Ara h 7 and 2 (AUC 0.83 and 0.81). EUROLINE intensity values showed a strong to very strong correlation with ISAC ISU results for the peanut storage proteins ($r_s$ value Ara h 1: 0.73, Ara h 2: 0.87, Ara h 3: 0.80, Ara h 6: 0.84, all p<0.001). Ara h 7 intensity values strongly correlated with those from Ara h 2 and 6 on EUROLINE ($r_s$=0.81 and p<0.001 for both). Sensitization results as well as discriminative ability for components on both EUROLINE and ImmunoCAP ISAC are listed in Table 2.

Co-sensitization to peanut storage proteins was most common. Almost half of all patients sensitized to peanut storage proteins Ara h 1, 2, 3, 6 or 7 was sensitized to all five (46%; Figure E1 in the Online Repository), followed by co-sensitization to Ara h 2, 6 and 7 only (14%). When looking specifically at patients sensitized to 2S albumins Ara h 2, 6 or 7, the majority was co-sensitized to all three (n=24, 68%; FIG. 1). Mono-sensitization was observed for Ara h 2 (n=6), Ara h 6 (n=2) and Ara h 7 (n=2), with a positive peanut challenge in 4 out of 6, 1 out of 2 and 1 out of 2 respectively.

ELISA Inhibition with Ara h 2, 6 and 7 Isoforms

For the 10 patients in the inhibition study, median age was 25 years and four were male. Sensitization to peanut extract was detected in all subjects, with ImmunoCAP titers ranging from 1.7 to >100 kU/L. Firstly, IgE reactivity against the three Ara h 7 isoforms, as well as Ara h 2 and 6 was assessed in the 10 sera by means of ELISA. Four sera showed reactivity to all five components. Additionally, two sera reacted to Ara h 7.0201, Ara h 2 and 6 and one serum to Ara h 2 and 6 only. In the remaining three patients OD values were too low for inhibition experiments. Optimal dilutions were determined for each serum (data not shown). The cross inhibition experiments illustrated that there was variability per patient serum in the maximum amount of inhibition obtained between the different 2S albumins (FIG. 3). In some patients, no inhibition was observed, while others demonstrated partly or almost complete inhibition with the different immobilized allergens and inhibitors. For both the Ara h 7.0101 and 7 isoforms, the other two isoforms were able to achieve strong inhibition, similar to inhibition with the same allergen. For Ara h 7.0201, inhibition with the other two epitopes resulted in very limited inhibition.

The variability in inhibition was even more pronounced between the different 2S albumins (FIG. 3). For example, for immobilized Ara h 7.0201, inhibition with Ara h 6 resulted in 8 to 86% inhibition (median 22%) and with Ara h 2 inhibition of 4 to 71% (median 16%). On the other hand, binding to Ara h 6 and Ara h 2 was inhibited by Ara h 7 isoforms, but inhibition of sIgE against Ara h 6 by Ara h 2 ranged from 12 to 70% (median 43%) and vice versa up to 77% (median 24%). In summary, Ara h 2 and 6 were able to inhibit binding to Ara h 7.0201 in some patients, but not others. The Ara h 7 isoforms were poorly able to inhibit binding to Ara h 2 and 6, although Ara h 2 and 6 were able to inhibit binding to each other in a varying degree.

Discussion

In our cohort of 80 peanut challenged patients, we demonstrated that Ara h 7.0201 has a discriminative ability very similar to the major allergens Ara h 2 and 6, which can be explained by their frequent co-sensitization, together with a strong correlation between their results. Overall, we found that Ara h 6 had the best discriminative ability, slightly higher than Ara h 2, on both ImmunoCAP ISAC as on the EUROLINE system.

Besides the common co-sensitization, we also observed mono-sensitization to Ara h 2, 6 or 7.0201. While mono-sensitization to Ara h 2 was most-common (n=6), it is important to acknowledge the presence of mono-sensitization to Ara h 6 and 7.0201, which would be missed when only testing for sensitization to Ara h 2. This is the first study demonstrating mono-sensitization to Ara h 7.0201 in two subjects.

Previous studies have investigated sensitization to Ara h 7, but only the Ara h 7 01.01 isoform. After first cloning Ara h 7.0101, Kleber-Janke et al. detected sensitization to rAra h 7.0101 in 17 out of 40 (43%) peanut sensitized subjects with a convincing history of peanut allergy, compared to 85% for Ara h 2. Codreanu and colleagues investigated the role of several recombinant peanut in an immunoassay and demonstrated that rAra h 7.0101 has a poor sensitivity compared to rAra h 2 and 6.

The inhibition experiments in our study illustrated that Ara h 7.0201 is the most relevant isoform of Ara h 7. In sera of patients with sIgE against Ara h 7.0101 and 7.0, strong inhibition by the other isoforms suggest recognition of epitopes present on all three Ara h 7 isoforms. On the other hand, in subjects sensitized to Ara h 7.0201 a lack of inhibition by the other isoforms indicate co-sensitization to unique epitopes, not present on the other two isoforms. In four of the six sera sensitized to any Ara h 7 isoform, there was co-sensitization to all three Ara h 7 isoforms. It appears contradicting that binding to Ara h 7.0201 could not be inhibited by the other isoforms, while the other way around Ara h 7.0201 was able to inhibit binding to the other isoforms. One explanation is recognition of multiple epitopes of Ara h 7.0201, both unique and cross-reactive, in a single patient, where abundant sIgE against the unique epitope(s) present on one Ara h 7 isoform result in low inhibition with other isoforms lacking that epitope. Another influencing factor could be the difference in accessibility of epitopes for IgE between the immobilized coated allergens on the solid phase versus the dissolved, folded allergens.

Cross-inhibition of 2S albumins showed that IgE against Ara h 2 and 6 could not be inhibited by Ara h 7 isoforms, but to some extend by each other. This could be explained by shared epitopes on Ara h 2 and 6 that are not part of Ara h 7 isoforms.

In conclusion, this study has demonstrated that Ara h 7 isotype 7.0201 is the third clinically relevant peanut 2S albumin, with on population level a discriminative ability for peanut allergy comparable to Ara h 2 and 6. While co-sensitization to peanut storage proteins, and more specifically 2S albumins, is most common, mono-sensitization to either Ara h 2, 6 or 7 occurs in individual patients, leading to a risk of misdiagnosis when testing for a single 2S albumin.

Example 4: Detection of IgE Antibodies Against Specific Ara h 7 Epitopes Using Peptide Microarrays Peptide Microarray Incubation and Visualization A peptide microarray comprising 15mer peptides of Ara h 7.0201 (SEQ ID NO2) with overlapping sequences (offset: 1, every peptide printed in duplicates) was commercially obtained (PEPperPRINT), covering the C-terminus of Ara h 7.0201 (SEQ ID NO6). For the incubation experiments the microarray was blocked with working strength universal buffer (WSUB, see example 2) for 1 h at RT on an orbital shaker. All further described incubations were also carried out in WSUB. Sera of 3 peanut positive and 2 peanut negative patients were diluted 1:4 and incubated overnight at 4° C. For the detection of bound IgE antibodies, biotinylated anti-IgE IT-28 (Squarix) was diluted 1:5000 and incubated on the array for 1 h at room temperature. After washing, the array was incubated for 1 h at room temperature with fluorescent Neutravidin 800 (Thermo Fisher), diluted 1:5000. The peptide microarray slides were scanned with a Licor Odyssey Imager at a wavelength of 800 nm (intensity:

8.5). Image focus was set to 0.8 mm and the maximum image resolution (21 μm) was chosen to guarantee maximum sensitivity.

Evaluation

After scanning. TIFF images and peptide map files were loaded to the Pepslide Analyzer Software (SICASYS) for quantitation of the signals corresponding to every single peptide. The raw data was exported as CSV files and the log 2 of the signal-to-noise ratio for each single Ara h 7 peptide ($S_{Ara}$) and for empty spots ($S_{Blank}$) on the array was calculated. For a more robust and normalized evaluation, z-scores for every single peptide (Zi) were calculated according to the following formula:

$$Z_i = \frac{S_i - \text{Median}(S_{Blank})}{MAD(S_{Blank})}$$

Based on those calculations, a positive binding epitope was defined as the detection of at least 6 subsequent peptides comprising a z-score of 3.0 or higher (p=0.003). Data visualization was performed using Microsoft Excel (FIG. 4).

Results

While no epitopes were detected by the two negative sera, using serum 3, a previously unknown Ara h 7.0201 epitope could be detected comprising the sequence GFRSPS (amino acids 129-134) (amino acid residue numbers according to SEQ ID NO2). Although below the z-score cutoff, this epitope is also detectable for serum 1. Since this sequence is unique to Ara h 7.0201, it can be concluded that this epitope is the one associated with the enhanced reactivity of Ara h 7.0201 compared to the two other isoforms.

Tables

TABLE 1

Peanut storage proteins present on the EUROLINE strip. Adapted from Becker and Jappe [5] and Van Erp et al [7].

| Allergen | Protein superfamily | Proportion of total protein | Sedimentation coefficient | (Assumed) biological function | Aliases |
| --- | --- | --- | --- | --- | --- |
| Ara h 1 | Cupin superfamily | 11-31% | 7S vicilin | Storage protein | Conarachin |
| Ara h 2 | Prolamin superfamily | 7-16% | 2S albumin | Storage protein, trypsin inhibitor | Conglutin |
| Ara h 3 | Cupin superfamily | 38-76% | 11S legumin, glycinin | Storage protein | Arachin |
| Ara h 6 | Prolamin superfamily | 4-14% | 2S albumin | Storage protein | Conglutin |
| Ara h 7 | Prolamin superfamily | 0.5% [16] | 2S albumin | Trypsin/amylase inhibitor [4], storage protein | Conglutin |

TABLE 2

Patient characteristics and sensitization data of the 40 peanut tolerant and 40 peanut allergic patients in the cohort

| Characteristic/ sensitization | Overall (n = 80) | Peanut tolerant (n = 40) | Peanut allergic (n = 40) | p value† | Tolerant versus allergic AUC (95% CI) | |
| --- | --- | --- | --- | --- | --- | --- |
| Age (median [IQR]) | 25 (21-37) | 31 (22-43) | 23 (20-29) | 0.01 | — | — |
| Sex (n male [%]) | 29 (36%) | 12 (30%) | 17 (43%) | 0.25 | — | — |
| EUROLINE* | | | | | | |
| Ara h 1 | 20 (25%) | 3 (8%) | 17 (43%) | <0.001 | 0.69 | (0.57-0.81) |
| Ara h 2 | 30 (38%) | 4 (10%) | 26 (65%) | <0.001 | 0.81 | (0.71-0.91) |
| Ara h 3 | 17 (21%) | 2 (5%) | 15 (38%) | <0.001 | 0.72 | (0.61-0.84) |
| Ara h 6 | 27 (34%) | 3 (8%) | 24 (60%) | <0.001 | 0.85 | (0.76-0.93) |
| Ara h 7 | 27 (34%) | 3 (8%) | 24 (60%) | <0.001 | 0.83 | (0.73-0.92) |

IQR: Interquartile range.
AUC: Area under the curve.
CI: confidence interval
*Using manufacturer's recommended cutoff values for a positive test.
†p value of difference in number of positive tests between tolerant and allergic subjects (chi-squared test).
‡ n = 79

TABLE 3

Individuell Dilution of the sera for dose dependent
inhibition experiment described in example 3

| Serum | ELISA coated with | | | | |
|---|---|---|---|---|---|
| No | Ara h 7.0101 | mAra h 7.0201 | Ara h 7.0 | Ara h 6.0101 | -Ara h 2.0201 |
| 1 | 1:5 | 1:5 | 1:5 | 1:5 | 1:5 |
| 2 | 1:5 | 1:10 | 1:5 | 1:20 | 1:10 |
| 3 | 1:5 | 1:10 | 1:5 | 1:10 | 1:5 |
| 4 | 1:5 | 1:5 | 1:5 | 1:5 | 1:5 |
| 5 | — | 1:5 | — | 1:5 | 1:5 |
| 6 | — | — | — | 1:5 | 1:5 |
| 7 | — | 1:5 | — | 1:5 | 1:5 |

The invention claimed is:

1. A diagnostically useful carrier, comprising:
a polypeptide comprising SEQ ID NO: 8 for specifically capturing an antibody to Ara h 7 isotype 7.0201 in a sample from a subject, wherein the antibody to Ara h 7 isotype 7.0201 binds to a sequence of SEQ ID NO: 6 that comprises SEQ ID NO: 8, and
a carrier, which is at least one member selected from the group consisting of a bead, a test strip, a microtiter plate, a microarray, a solid polymer derived from cellulose, a line blot, a dot blot, a glass surface, a slide, and a biochip,
wherein the polypeptide is immobilized on the diagnostically useful carrier.

2. The diagnostically useful carrier according to claim 1, further comprising:
a polypeptide for specifically capturing an antibody to at least one further antigen selected from the group consisting of Ara h 2, Ara h 6, Ara h 1, Ara h 3, Ara h 9, Ara h 8, and Ara h 5.

3. A method, comprising:
obtaining a sample from a subject; and
detecting, in the sample, the presence of an antibody to Ara h 7 isotype 7.0201 that binds to a sequence of SEQ ID NO: 6 that comprises SEQ ID NO: 8 by
contacting the sample with the diagnostically useful carrier according to claim 1, or
contacting the sample with a diagnostically useful carrier comprising an immobilized antibody capable of binding to the antibody to Ara h 7 isotype 7.0201 and with a polypeptide for specifically binding to the antibody to Ara h 7 isotype 7.0201, wherein. the polypeptide comprises a member selected from the group consisting of SEQ ID NO: 6, SEQ ID NO: 7, SEQ ID NO: 8, SEQ ID NO: 9 and SEQ ID NO: 10; and
detecting binding between the polypeptide of the diagnostically useful carrier and the antibody to Ara h 7 isotype 7.0201.

4. The method according to claim 3, further comprising:
detecting, in a sample from a subject, the presence of an antibody to at least one further antigen.

5. The method according to claim 3, wherein
the presence or absence of the antibody to Ara h 7 isotype 7.0201 and the presence of an antibody to at least one further antigen are detected simultaneously.

6. The method according to claim 3, wherein
the presence or absence of the antibody to Ara h 7 isotype 7.0201 and the presence of an antibody to at least one further antigen are detected in spatially separate binding reactions.

7. The method according to claim 3, wherein
the presence of the antibody Ara h 7 isotype 7.0201 and the presence of an antibody to at least one further antigen are detected in a one-pot reaction.

8. The method according to claim 3, wherein
the presence or absence of the antibody to Ara h 7 isotype 7.0201, and the presence of an antibody to at least one of Ara h 2 and Ara h 6, are detected simultaneously.

9. The method according to claim 5, wherein
the immobilized antibody is an IgE antibody.

10. The method according to claim 5, wherein the immobilized antibody binding to the antibody to Ara h 7 isotype 7.0201 is an antibody that recognizes IgE, IgG, or IgA class antibodies.

11. The method according to claim 5, wherein the antibody to Ara h 7 isotype 7.0201 binds to the amino acid sequence selected from the group consisting of SEQ ID NO: 6, SEQ ID NO: 7, SEQ ID NO: 8, SEQ ID NO: 9, and SEQ ID NO: 10.

12. The carrier according to claim 1, wherein
the antibody to isotype 7.0201 is an antibody monospecific to Ara h 7.

13. A method of making a kit, the method comprising:
adding the diagnostically useful carrier according to claim 1 to a container, said container comprising:
a device for receiving a bodily fluid sample from a subject.

14. The diagnostically useful carrier according to claim 1, wherein
the antibody to Ara h 7 isotype 7.0201 is an antibody to SEQ ID NO: 6; or
the antibody to Ara h 7 isotype 7.0201 is an antibody to at least one member selected from the group consisting of SEQ ID NO: 7, SEQ ID NO: 8, SEQ ID NO: 9, and SEQ ID NO: 10; or
the antibody to Ara h 7 isotype 7.0201 is an antibody to SEQ ID NO: 8.

15. The diagnostically useful carrier according to claim 1, further comprising:
a polypeptide for specifically capturing an antibody to at least one further antigen selected from the group consisting of Ara h 2, Ara h 6, Ara h 1, Ara h 3, and Ara h 9.

16. The diagnostically useful carrier according to claim 1, wherein the carrier is at least one member selected from the group consisting of a microtiter plate and a line blot.

17. The diagnostically useful carrier according to claim 1, wherein
the antibody to Ara h 7 isotype 7.0201 is at least one member selected from the group consisting of IgA, IgG, and IgE; or
the antibody to Ara h 7 isotype 7.0201 is at least one member selected from the group consisting of IgG and IgE; or
the antibody to Ara h 7 isotype 7.0201 is at least one member selected from the group consisting of IgG1, IgG4, and IgE.

18. A vaccine, comprising:
a polypeptide comprising a sequence of SEQ ID NO: 6 that comprises SEQ ID NO: 8, an adjuvant, and at least one diluent, at least one glidant, and/or at least one filling agent.

19. The vaccine according to claim 11, wherein
the diluent is at least one member selected from the group consisting of starch, lactose, microcrystalline cellulose, and dicalcium phosphate.

20. A kit, comprising:
a diagnostically useful carrier, and
a labelled antigen that is recognized by an antibody to Ara h 7 isotype 7.0201, wherein the labelled antigen is selected from the group consisting of a sequence of SEQ ID NO: 6, SEQ ID NO: 7, SEQ ID NO: 8, SEQ ID NO: 9, and SEQ ID NO: 10;
wherein the diagnostically useful carrier comprises:
a carrier having an immobilized antibody that recognizes and immobilizes IgE, IgG, or IgA class antibodies, wherein the IgE, IgG, or IgA class antibodies comprise the antibody to Ara h 7 isotype 7.0201, and
said carrier selected from the group consisting of a bead, a test strip, a microtiter plate, a microarray, a solid polymer derived from cellulose, a line blot, a dot blot, a glass surface, a slide, a biochip, and a membrane.

21. The kit according to claim 20, wherein the kit comprises one or more selected from the group consisting of a sample dilution buffer, a washing buffer, a positive control, a negative control, and a standard solution for preparing a calibration curve.

22. The kit according to claim 20, wherein the labelled antigen comprises a label selected from the group consisting of a fluorescent label, a radioactive label, a chemiluminescent label.

23. The kit of claim 20, wherein the antibody to Ara h 7 isotype 7.0201 binds to a sequence of SEQ ID NO: 6.

* * * * *